(12) United States Patent
Varhaniovsky

(10) Patent No.: US 7,574,845 B2
(45) Date of Patent: Aug. 18, 2009

(54) BEVERAGE BOTTLING PLANT FOR FILLING BEVERAGE BOTTLES HAVING A BOTTLE HANDLING STATION AND A METHOD OF OPERATION THEREOF

(75) Inventor: Gyula Varhaniovsky, Waltrop (DE)

(73) Assignee: KHS Maschinen- und Anlagenbau AG, Dortmund (DE)

( * ) Notice: Subject to any disclaimer, the term of this patent is extended or adjusted under 35 U.S.C. 154(b) by 204 days.

(21) Appl. No.: 11/624,469

(22) Filed: Jan. 18, 2007

(65) Prior Publication Data

US 2007/0163212 A1    Jul. 19, 2007

(30) Foreign Application Priority Data

Jan. 19, 2006    (DE) ........................ 10 2006 002 633

(51) Int. Cl.
  *B65B 57/00*    (2006.01)
  *B65B 55/10*    (2006.01)
  *G01N 21/90*    (2006.01)

(52) U.S. Cl. ............................. 53/426; 53/471; 53/167; 53/282; 53/52; 356/239.5

(58) Field of Classification Search .............. 356/239.5, 356/239.4; 53/167, 426, 52–54, 471, 282
See application file for complete search history.

(56) References Cited

U.S. PATENT DOCUMENTS

| | | | | |
|---|---|---|---|---|
| 4,083,637 A | * | 4/1978 | Ellinger et al. ........... | 356/239.4 |
| 4,207,974 A | * | 6/1980 | Dragotta ..................... | 198/384 |
| 4,209,802 A | | 6/1980 | Fogg et al. | |
| 5,405,014 A | * | 4/1995 | Krieg et al. ................. | 209/524 |
| 5,528,036 A | * | 6/1996 | Achter et al. .......... | 250/339.12 |
| 5,713,403 A | * | 2/1998 | Clusserath et al. .......... | 141/101 |
| 5,896,899 A | * | 4/1999 | Schmitz ....................... | 141/92 |
| 6,012,344 A | * | 1/2000 | Halbo ....................... | 73/865.8 |

FOREIGN PATENT DOCUMENTS

| | | | |
|---|---|---|---|
| EP | 0 655 621 A1 | | 5/1995 |
| EP | 0 797 092 B1 | | 9/1997 |
| EP | 871028 A1 | * | 10/1998 |
| FR | 2 746 502 A1 | | 9/1997 |
| JP | 8-210992 A | * | 8/1996 |
| JP | 9-269300 A | * | 10/1997 |
| JP | 11-344452 A | * | 12/1999 |
| JP | 2004226071 A | * | 8/2004 |
| WO | WO 01/44 791 A2 | | 6/2001 |

\* cited by examiner

*Primary Examiner*—Stephen F Gerrity
(74) *Attorney, Agent, or Firm*—Nils H. Ljungman & Associates

(57) ABSTRACT

A beverage bottling plant for filling beverage bottles having a bottle handling station and a method of operation thereof. The bottle handling station has an inspection station for inspecting bottles for observable contaminants that have been rinsed off of the interior of the bottles using an amount of liquid introduced into the bottles by a liquid dispenser, and then gathered in the amount of liquid in a bottom area of the bottles.

19 Claims, 11 Drawing Sheets

BEVERAGE BOTTLING PLANT FOR FILLING BEVERAGE BOTTLES HAVING A BOTTLE HANDLING STATION AND A METHOD OF OPERATION THEREOF

BACKGROUND

1. Technical Field

This application relates to a beverage bottling plant for filling beverage bottles having a bottle handling station and a method of operation thereof.

2. Background Information

A beverage bottling plant for filling bottles with a liquid beverage filling material can possibly comprise a beverage filling machine, which is often a rotary filling machine, with a plurality of beverage filling positions, each beverage filling position having a beverage filling device for filling bottles with liquid beverage filling material. The filling devices may have an apparatus designed to introduce a predetermined volume of liquid beverage filling material into the interior of bottles to a substantially predetermined level of liquid beverage filling material.

Some beverage bottling plants may possibly comprise filling arrangements that receive a liquid beverage material from a toroidal or annular vessel, in which a supply of liquid beverage material is stored under pressure by a gas. The toroidal vessel may also be connected to at least one external reservoir or supply of liquid beverage material by a conduit or supply line. In some circumstances it may even be possible that a beverage bottling plant has two external supply reservoirs, each of which may be configured to store either the same liquid beverage product or different products. These reservoirs could possibly be connected to the toroidal or annular vessel by corresponding supply lines, conduits, or other arrangements. It is also possible that the external supply reservoirs could be in the form of simple storage tanks, or in the form of liquid beverage product mixers.

A wide variety of types of filling elements are used in filling machines in beverage bottling or container filling plants for dispensing a liquid product into bottles, cans or similar containers, including but not limited to filling processes that are carried out under counterpressure for the bottling of carbonated beverages. The apparatus designed to introduce a predetermined flow of liquid beverage filling material further comprises an apparatus that is designed to terminate the filling of the beverage bottles upon the liquid beverage filling material reaching the predetermined level in bottles. There may also be provided a conveyer arrangement that is designed to move bottles, for example, from an inspecting machine to the filling machine.

After a filling process has been completed, the filled beverage bottles are transported or conveyed to a closing machine, which is often a rotary closing machine. A revolving or rotary machine comprises a rotor, which revolves around a central, vertical machine axis. There may further be provided a conveyer arrangement configured to transfer filled bottles from the filling machine to the closing station. A transporting or conveying arrangement can utilize transport star wheels as well as linear conveyors. A closing machine closes bottles by applying a closure, such as a screw-top cap or a bottle cork, to a corresponding bottle mouth. Closed bottles are then usually conveyed to an information adding arrangement, wherein information, such as a product name or a manufacturer's information or logo, is applied to a bottle. A closing station and information adding arrangement may be connected by a corresponding conveyer arrangement. Bottles are then sorted and packaged for shipment out of the plant.

Many beverage bottling plants may also possibly comprise a rinsing arrangement or rinsing station to which new, non-return and/or even return bottles are fed, prior to being filled, by a conveyer arrangement, which can be a linear conveyor or a combination of a linear conveyor and a starwheel. Downstream of the rinsing arrangement or rinsing station, in the direction of travel, rinsed bottles are then transported to the beverage filling machine by a second conveyer arrangement that is formed, for example, by one or more starwheels that introduce bottles into the beverage filling machine.

It is a further possibility that a beverage bottling plant for filling bottles with a liquid beverage filling material can be controlled by a central control arrangement, which could be, for example, a computerized control system that monitors and controls the operation of the various stations and mechanisms of the beverage bottling plant.

Many different configurations of devices currently exist for the inspection of bottles in which the bottles are moved past at least one inspection station or one inspection module and in which inspection takes place optoelectrically, and possibly with the use of at least one light source and at least one optoelectric sensor unit, e.g. an optoelectric detector or a camera.

OBJECT OR OBJECTS

An object of at least one possible embodiment of the present application is to describe a device which essentially makes possible a substantially reliable inspection of bottles or similar containers that are made of a translucent or transparent material (e.g. glass or a translucent plastic, such as PET for example), even including possible inspection of essentially critical areas of containers.

SUMMARY

At least one possible embodiment of the present application teaches a method for inspection of bottles or similar containers that are made of a translucent or even transparent material, in which containers can be moved on a conveyor line in a transport direction past at least one possible inspection station, wherein the containers, which can be fed to a machine standing in an substantially upright position, may be pivoted during transport on the conveyor line and possibly moved past at least one inspection module in an essentially pivoted position.

Another possible embodiment of the present application describes a device for inspection of bottles or similar containers that are made of a translucent or even transparent material, with a conveyor element with at least two conveyor belts that can possibly be driven in circulation and each may form a closed loop, each of which may forms with at least one conveyor belt length a conveyor line on which the containers are moved between the conveyor belt lengths held in a clamped seat in a transport direction A, wherein by means on the conveyor line to pivot the containers that are fed in the upright position to a container inlet of the conveyor line and removed at a container outlet of the conveyor line in the upright position, at least once between the container inlet and the container outlet in the plane perpendicular to the transport direction.

At least one possible feature of the present application is that containers, as they are being transported in an initially substantially upright container position in which the containers are fed to the device on the conveyor element of the device, are inclined, i.e. pivoted from a container position in which the containers are oriented with their container axis in the vertical direction and are tilted for the inspection such that the inclined containers lie with their container axis in a plane that is perpendicular to the direction of transport, although the container axis encloses an angle with the vertical. After the inspection or after the containers have passed the at least one inspection station or the final inspection station in the transport direction, the containers on the conveyor line are once again pivoted back into their upright container position.

As a result of the inclined position of the containers during the inspection and as they pass the at least one inspection station, it is possible, among other things, to reliably inspect critical areas of the containers, for example the transition between a container bottom and a container peripheral wall. It is also possible as a result of the inclined position to introduce a liquid, for example a test liquid (e.g. sterile water into the initially empty container for the inspection, which absorbs and/or carries away with it any foreign matter or foreign bodies that may be present in the container before the inspection, and which then collect at the transition between the bottom of the container and the container peripheral wall as a result of the inclined position of the container. As the container passes through the at least one inspection station or the at least one inspection module, the liquid can then be tested or analyzed for any foreign matter or foreign objects, for example by means of an optoelectric test. On account of the inclined position of the container, only a small quantity of liquid is necessary, and therefore any foreign matter will be present in an elevated concentration in the liquid, which means that clear and unambiguous results can be achieved.

The above-discussed embodiments of the present application will be described further hereinbelow. When the word "application" or "embodiment of the application" is used in this specification, the word "application" or "embodiment of the application" includes "applications" or "embodiments of the application", that is the plural of "application" or "embodiment of the application". By stating "application" or "embodiment of the application", the Applicant does not in any way admit that the present application does not include more than one patentably and non-obviously distinct possible embodiment of the present application, and maintains that this application may include more than one patentably and non-obviously distinct possible embodiment of the present application. The Applicant hereby asserts that the disclosure of this application may include more than one possible embodiment of the present application, and, in the event that there is more than one possible embodiment of the present application, that these possible embodiments of the present applications may be patentable and non-obvious one with respect to the other. Developments of at least one possible embodiment are described in the dependent claims.

BRIEF DESCRIPTION OF THE DRAWINGS

At least one possible embodiment of the present application is explained in greater detail below on the basis of the exemplary embodiments that are illustrated in the accompanying figures. In the figures.

DESCRIPTION OF EMBODIMENT OR EMBODIMENTS

Figure 1:
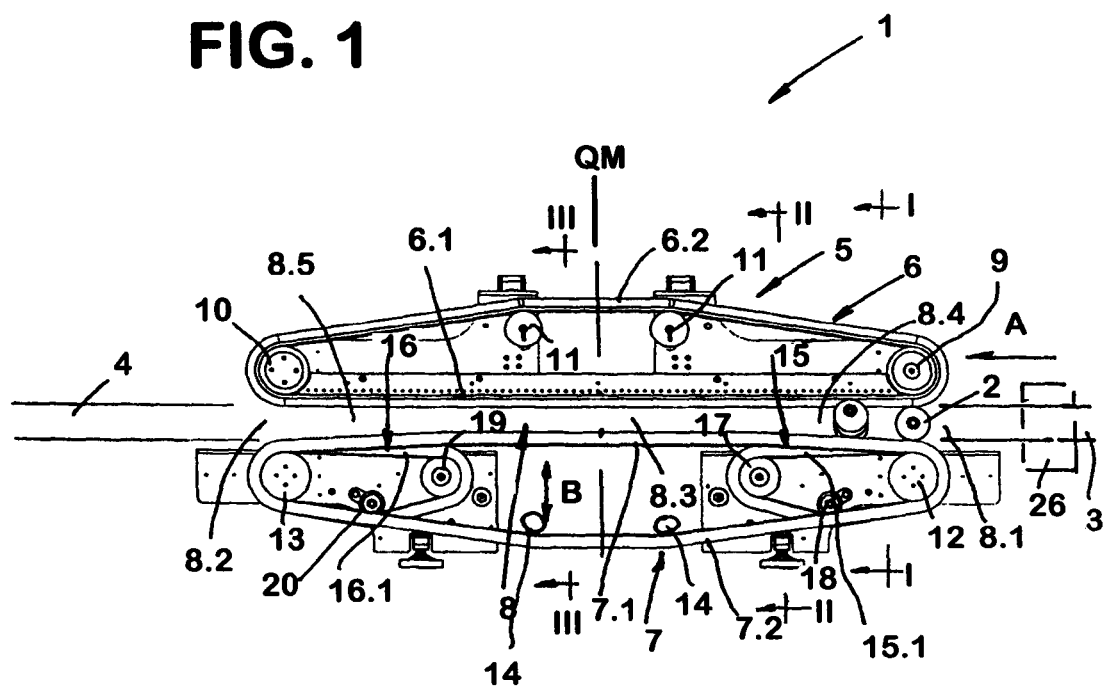
FIG. 1 is a simplified drawing in an overhead view of a device for the inspection of bottles.
Figure 1A:
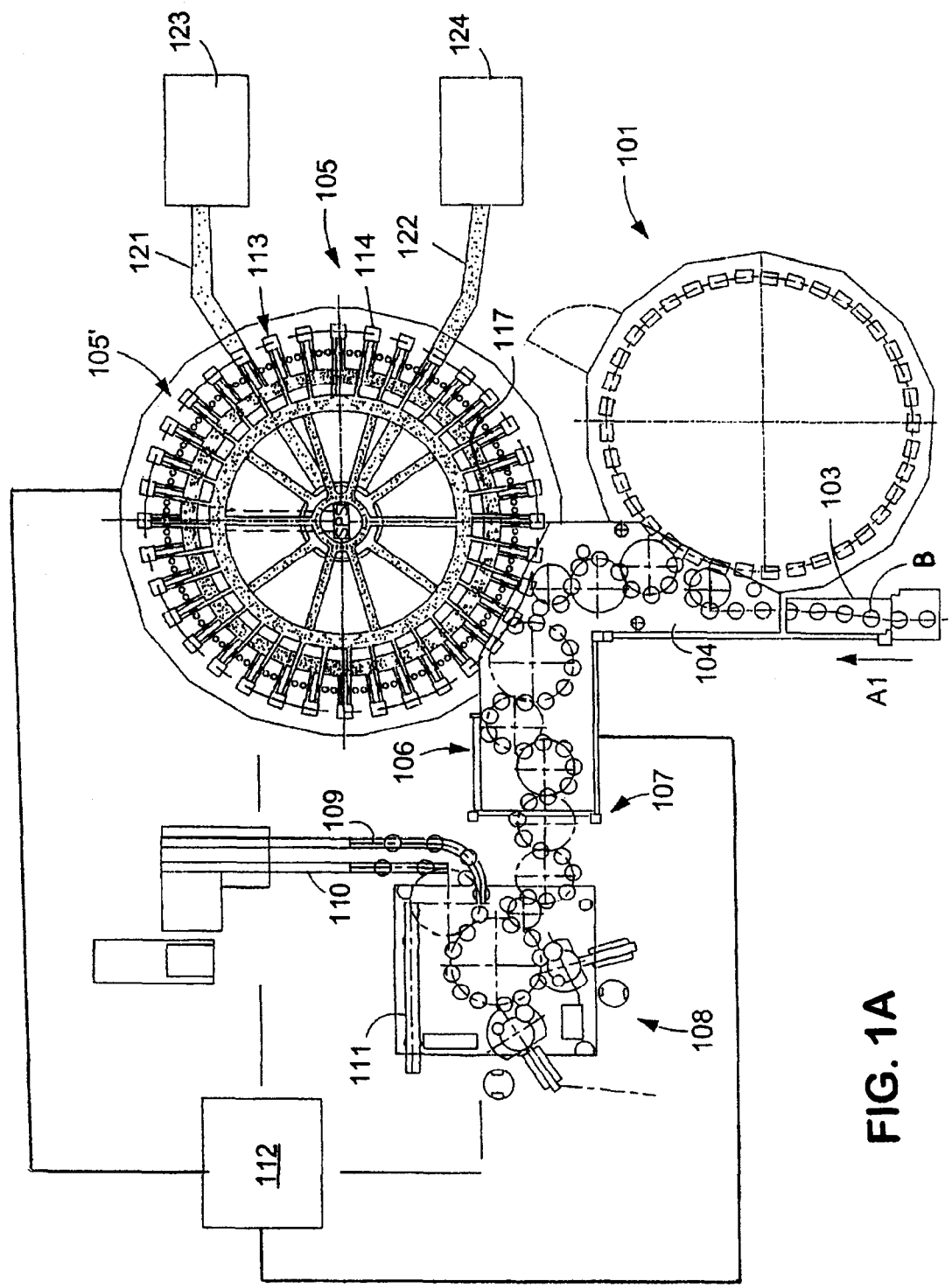
FIG. 1A shows schematically the main components of one possible embodiment example of a system for filling containers.

FIG. 1A shows schematically the main components of one possible embodiment example of a system for filling containers, specifically, a beverage bottling plant for filling bottles B with at least one liquid beverage, in accordance with at least one possible embodiment, in which system or plant could possibly be utilized at least one aspect, or several aspects, of the embodiments disclosed herein.

FIG. 1A shows a rinsing arrangement or rinsing station 101, to which the containers, namely bottles B, are fed in the direction of travel as indicated by the arrow A1, by a first conveyer arrangement 103, which can be a linear conveyor or a combination of a linear conveyor and a starwheel. Downstream of the rinsing arrangement or rinsing station 101, in the direction of travel as indicated by the arrow A1, the rinsed bottles B are transported to a beverage filling machine 105 by a second conveyer arrangement 104 that is formed, for example, by one or more starwheels that introduce bottles B into the beverage filling machine 105.

The beverage filling machine 105 shown is of a revolving or rotary design, with a rotor 105', which revolves around a central, vertical machine axis. The rotor 105' is designed to receive and hold the bottles B for filling at a plurality of filling positions 113 located about the periphery of the rotor 105'. At each of the filling positions 103 is located a filling arrangement 114 having at least one filling device, element, apparatus, or valve. The filling arrangements 114 are designed to introduce a predetermined volume or amount of liquid beverage into the interior of the bottles B to a predetermined or desired level.

The filling arrangements 114 receive the liquid beverage material from a toroidal or annular vessel 117, in which a supply of liquid beverage material is stored under pressure by a gas. The toroidal vessel 117 is a component, for example, of the revolving rotor 105'. The toroidal vessel 117 can be connected by means of a rotary coupling or a coupling that permits rotation. The toroidal vessel 117 is also connected to at least one external reservoir or supply of liquid beverage material by a conduit or supply line. In the embodiment shown in FIG. 1A, there are two external supply reservoirs 123 and 124, each of which is configured to store either the same liquid beverage product or different products. These reservoirs 123, 124 are connected to the toroidal or annular vessel 117 by corresponding supply lines, conduits, or arrangements 121 and 122. The external supply reservoirs 123, 124 could be in the form of simple storage tanks, or in the form of liquid beverage product mixers, in at least one possible embodiment.

As well as the more typical filling machines having one toroidal vessel, it is possible that in at least one possible embodiment there could be a second toroidal or annular vessel which contains a second product. In this case, each filling arrangement 114 could be connected by separate connections to each of the two toroidal vessels and have two individuallycontrollable fluid or control valves, so that in each bottle B, the first product or the second product can be filled by means of an appropriate control of the filling product or fluid valves.

Downstream of the beverage filling machine 105, in the direction of travel of the bottles B, there can be a beverage bottle closing arrangement or closing station 106 which closes or caps the bottles B. The beverage bottle closing arrangement or closing station 106 can be connected by a third conveyer arrangement 107 to a beverage bottle labeling arrangement or labeling station 108. The third conveyor arrangement may be formed, for example, by a plurality of starwheels, or may also include a linear conveyor device.

In the illustrated embodiment, the beverage bottle labeling arrangement or labeling station 108 has at least one labeling unit, device, or module, for applying labels to bottles B. In the embodiment shown, the labeling arrangement 108 is connected by a starwheel conveyer structure to three output conveyer arrangements: a first output conveyer arrangement 109, a second output conveyer arrangement 110, and a third output conveyer arrangement 111, all of which convey filled, closed, and labeled bottles B to different locations.

The first output conveyer arrangement 109, in the embodiment shown, is designed to convey bottles B that are filled with a first type of liquid beverage supplied by, for example, the supply reservoir 123. The second output conveyer arrangement 110, in the embodiment shown, is designed to convey bottles B that are filled with a second type of liquid beverage supplied by, for example, the supply reservoir 124. The third output conveyer arrangement 111, in the embodiment shown, is designed to convey incorrectly labeled bottles B. To further explain, the labeling arrangement 108 can comprise at least one beverage bottle inspection or monitoring device that inspects or monitors the location of labels on the bottles B to determine if the labels have been correctly placed or aligned on the bottles B. The third output conveyer arrangement 111 removes any bottles B which have been incorrectly labeled as determined by the inspecting device.

The beverage bottling plant can be controlled by a central control arrangement 112, which could be, for example, computerized control system that monitors and controls the operation of the various stations and mechanisms of the beverage bottling plant.

The device designated 1 in the figures is used for the inspection of bottles 2 that are made of a translucent material, and specifically in the illustrated embodiment is used for the inspection of plastic bottles or PET bottles that have a concavely curved bottom 2.2 on the outside of the bottle opposite the bottle mouth 2.1.

The bottles 2 are fed to the device A in the transport direction A by means of a conveyor 3 that is realized in a suitable manner in the form of a single-track row of bottles in the upright position, i.e. with the bottle axis FA oriented in the vertical direction. After the inspection, the bottles 2 are in turn fed in the upright position to a conveyor 4, by means of which the bottles 2 are transported onward to another application, and specifically with the rejection as unacceptable of those bottles that were found to contain foreign objects, foreign matter etc.

A central element of the device 1 is a conveyor element 5 which, among other things, has two circulating conveyor belts 6 and 7 that are driven in an endless loop and each of which forms a closed loop, forming a conveyor line 8 on which the bottles 2 are moved in the transport direction A in a clamped position between the two conveyor belts 5 and 6 and are connected with a container inlet 8.1 on the outer conveyor 3 and downstream of which is the outer conveyor 4.

In the illustrated embodiment, the conveyors 3 and 4 as well as the conveyor line 8 are located in a line with reference to their transport direction A.

The conveyor belt 6 runs in the vicinity of the container inlet 8.1 over a guide pulley 9 and in the vicinity of the container outlet over a driven pulley 10, so that a conveyor belt length 6.1 is located on one side of the conveyor line 8. The conveyor belt 6 runs over two deflector or tensioning rolls 11 with a length 6.2 that lies at some distance from the conveyor line 8.

The conveyor belt 7 runs in an equivalent manner in the vicinity of the container inlet 18 over a guide pulley 12 and in the vicinity of the container outlet 8.2 over a driven pulley 13, so that it has a conveyor belt length 7.1 on the other side of the conveyor line 8 and extends over the entire length of the conveyor line 8. Guide means (not shown), in the form of friction guides or additional rollers, for example, are used to realize the length 7.1 so that it is non-linear, but has a curve so that in the illustration presented as FIG. 1, the distance between the length 7.1 and the length 6.1 initially decreases, beginning from the container inlet 8.1 in the transport direction A, is then constant in a middle segment of the conveyor line 8, and then again widens slightly toward the container outlet 8.1 The conveyor line 8 therefore forms three segments, namely a middle segment 8.3 that has an essentially constant distance between the two conveyor belt lengths 6.1 and 7.1, a segment 8.4 in which this distance decreases from the container inlet 8.1 toward the middle segment 8.3, and a segment 8.5 in which the distance between the conveyor belt lengths 6.1 and 7.1 increases again, beginning from the end of the middle segment 8.3 toward the container outlet 8.2.

The length 7.2 of the conveyor belt 7 that is farther from the conveyor line 8 is again guided over two deflector or tensioning rollers 14. All of the pulleys and rollers 9-11 and 12-14 are oriented with their axes in the vertical direction. The conveyor belts 6 and 7 are in particular also oriented on edge in the vicinity of their respective lengths 6.1, 6.2 and 7.1, 7.2.

As shown in FIG. 2-5, the conveyor belts 6 and 7 have a cross section in a shape such that each conveyor belt, on the inside of its loop, has an inner surface which is oriented vertically or approximately vertically and perpendicular to the direction of circulation of the conveyor belt 6 or 7 respectively, while the outside surface or container clamping surface of the conveyor belts 6 and 7 that form the outside of the loops is inclined with respect to the vertical perpendicular to the direction of circulation of the conveyor belts or perpendicular to the transport direction A. Consequently, the outer surface of the conveyor belt 6 on the conveyor belt length 6.1 encloses an angle $\alpha < 45°$, for example an angle on the order of magnitude between 20° and 25° with the vertical, which opens upward. The outer surface of the conveyor belt 7, in particular including over the length 7.1 encloses an angle $\beta$ with the vertical which is equal to or approximately equal to the angle $\alpha$ but opens downward, so that the two conveyor belts 6 and 7 are oriented with the outer surfaces of the their lengths 6.1 and 7.1 on both sides of the conveyor line 8 parallel or essentially parallel to each other, although the center plane between these outer surfaces is inclined at the angle $\alpha$ with respect to the vertical. In the vicinity of the container inlet 8.1 and also of the container outlet 8.2, support or auxiliary belts 15 and 16 respectively are provided below the conveyor belt 7. Both support belts are each realized in the form of endless circulating belts and belts that form a closed loop. The support belt 15 is guided in the vicinity of the container inlet 8.1 over a guide pulley that is not shown in the figures, which in the presentation selected for FIG. 1 is provided underneath the guide pulley 12 and is in a drive connection with this guide pulley 12, and also has the same diameter as the guide pulley 12. The support belt 15 is also guided over a guide pulley 17 and a tensioning roller, and specifically such that the support belt 15 forms a length 15.1 which, beginning from the container inlet 8.1, runs approximately to the beginning of the middle segment 8.3 of the conveyor line 8. All the pulleys and rollers of the support belt 15 are in turn oriented with their axes in the vertical direction.

The support belt 16 is located and oriented in mirror symmetry to the support belt 15 with reference to a vertical transverse center plane QM that is oriented perpendicular to the transport direction A, i.e. the support belt 16 that forms the endless circulating driven loop is guided over a pulley that is located underneath the pulley 13 and is in a drive connection with the pulley 13 as well as over a guide pulley 19 and a tensioning roller 20, and specifically so that the support belt 16 extends with the length 16.1 on the side of the segment 8.5 of the conveyor line 8, starting from the end of the middle area 8.3 to the container outlet 8.2. In the illustrated embodiment, the conveyor element 5 is also in mirror symmetry overall with the transverse center plane QM. The two conveyor belts 6 and 7 are driven synchronously so that the conveyor belt lengths 6.1 and 7.1 move at the same speed in the transport direction A. The support belts 15 and 16 are also driven so that their lengths 15.1 an 16.1 each move in the same direction and at the same speed as the conveyor belt length 7.1. In at least one possible embodiment, the speeds at which the conveyors 6 and 7 move may be different in order to cause rotation of the bottles or containers and promote or cause stirring of a liquid in the bottles.

Figure 3:
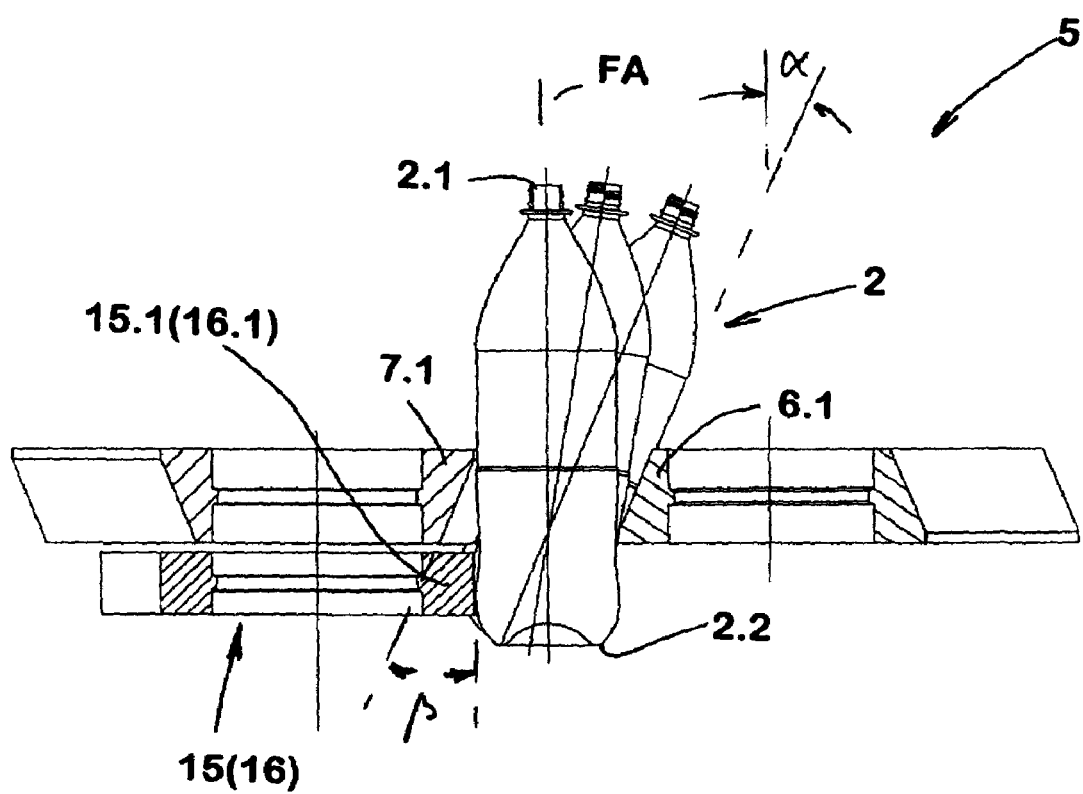
FIGS. 3-5 are sectional drawings along Lines I-I, II-II and III-III in FIG. 1, each with bottles located on the conveyor element.

As shown in FIG. 3, the bottles 2 at the container inlet 8.1 are transferred from the conveyor line 3 to the conveyor line 8 so that each bottle is held in a clamped position between the lower longitudinal edge of the conveyor belt length 6.1 on the one side of the conveyor line 8 and between the upper longitudinal edge of the conveyor belt length 7.1 and of the support belt length 15.1 on the other side of the conveyor line 8 in the vicinity of the bottom shell 2.3, and specifically so that the bottles 2 are also initially oriented with their bottle axis FA in the vertical direction with their bottom 2.2 above the conveyor element 5 and above the plane of the underside of the support belt 15 and project outward from the loop formed by this support belt.

There is an increasing inclination or tilt of the bottles 2 during the movement of the bottles 2 on the segment 8.4 as a result of the profile of the conveyor belt length 6.1, and specifically so that each bottle 2 continues to be held in its shell area 2.3 between the lower edge of the conveyor belt length 6.1 on the one hand and the upper edge of the conveyor belt length 7.1 and the support belt length 15.1 on the other hand. When it reaches the center segment 8.3, each bottle 2 is then still clamped only between the two conveyor belt lengths 6.1 and 7.1 and their inclined outer surfaces on the bottle shell 2.3, so that each bottle 2 is transported along the middle area 8.3 in the inclined position, in which the bottle axis FA lies in a plane that is oriented perpendicular to the transport direction A, but encloses the angle α with the vertical.

Figure 4:
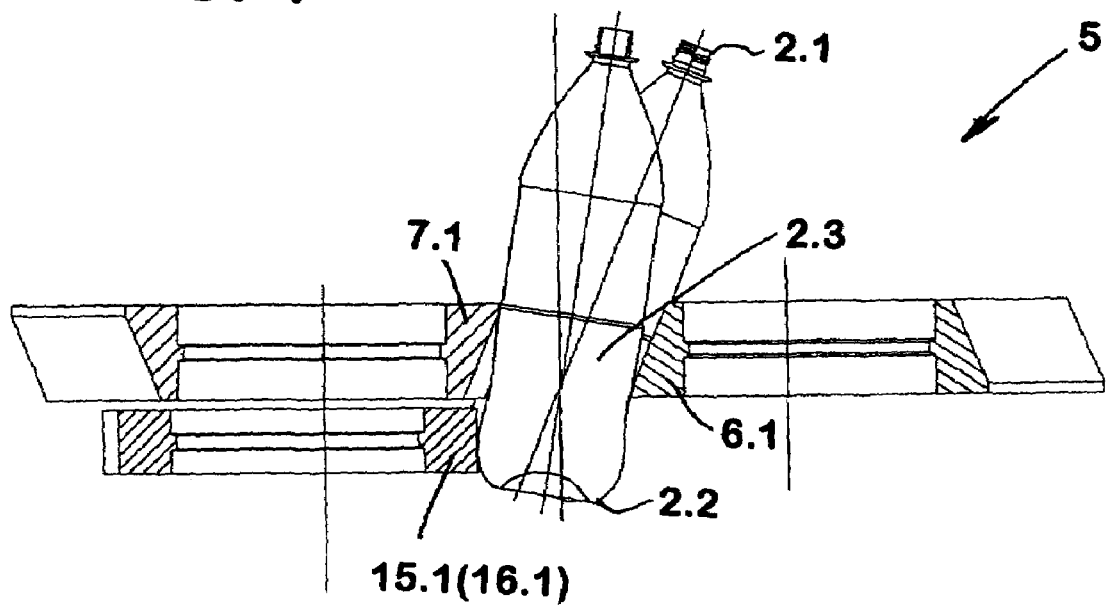

After passing the middle segment 8.3, each bottle is increasingly moved toward the upright position as it transported onward to the segment 8.5, which is realized so that it is in mirror symmetry to the segment 8.4 with reference to the transverse center plane QM. The bottles 2 are thereby held on the segment 8.5 in the same manner as shown in FIG. 4, and are then held upright in the area of the container outlet 8.2 and as shown in FIG. 3 between the conveyor belts 6 and 7 and are transferred to the conveyor 4 with additional support by the support belt 16.

It goes without saying that the distance between the conveyor belt length 6.1 and the conveyor belt length 7.1 and the support belt lengths 15.1 and 16.1 respectively are essentially always or generally selected so that each bottle 2 is securely held on the conveyor line 8 by fixed clamping on the shell 2.3. To achieve this stability, the conveyor belts 6 and 7 as well as the auxiliary belts 15 and 16 are realized so that they have sufficiently elasticity. The conveyor belt length 6.1 is also in at least one possible embodiment supported on the inside by one or more flexible support elements.

Figure 1B:
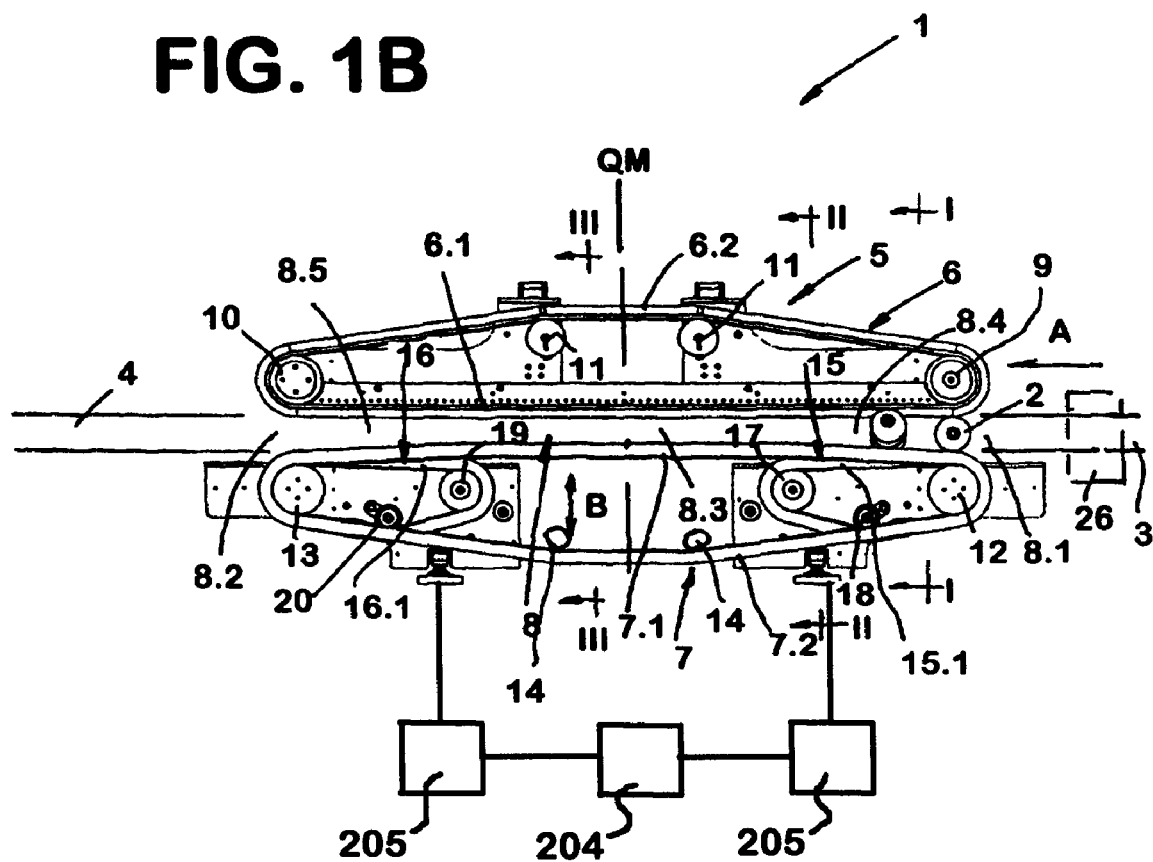
FIG. 1B shows a view of FIG. 1 with additional features according to at least one possible embodiment.
Figure 2:
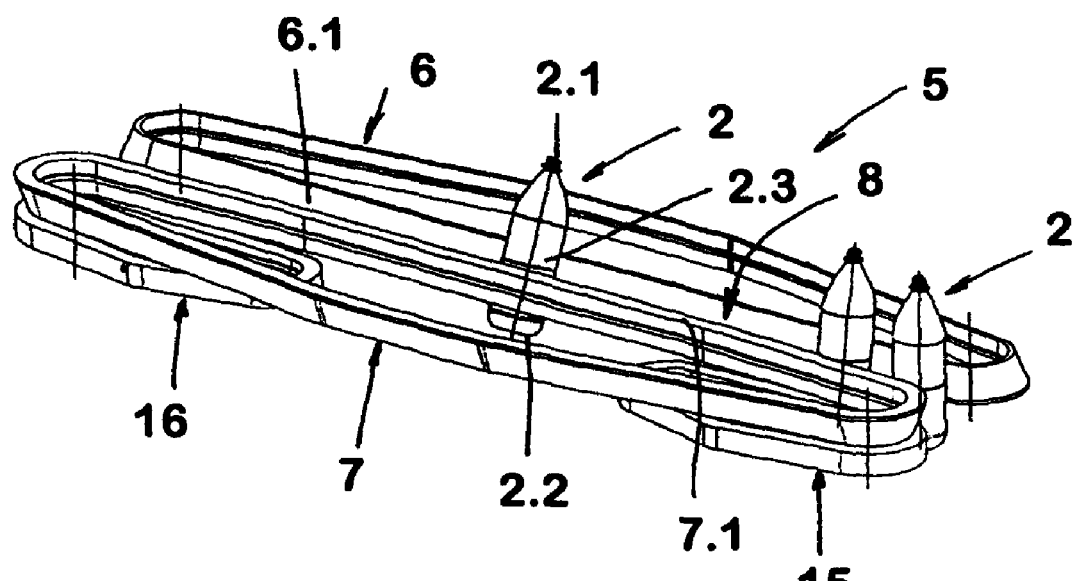
FIG. 2 is a schematic drawing in perspective of a conveyor or a conveyor element of the device illustrated in FIG. 1.

To adapt the device 1 for use with bottles 2 that have a different diameter, in the illustrated embodiment the conveyor belt 7 can be adjusted with the corresponding guide pulleys 12 and 13 and the guide rollers 14 and together with the two support belts 15 and 16 and their guide pulleys 17 and 19 respectively and tensioning rollers 18 and 20 respectively in the horizontal direction and perpendicular to the transport direction A, as indicated by the double arrow B. This adaptation can be performed manually, or can be controlled and performed automatically by a computer control system 204, as shown in FIG. 1B. The control system 204 activates drive devices 205 that perform the above-described adjustment to permit the handling of bottles or containers of different sizes.

Figure 5:
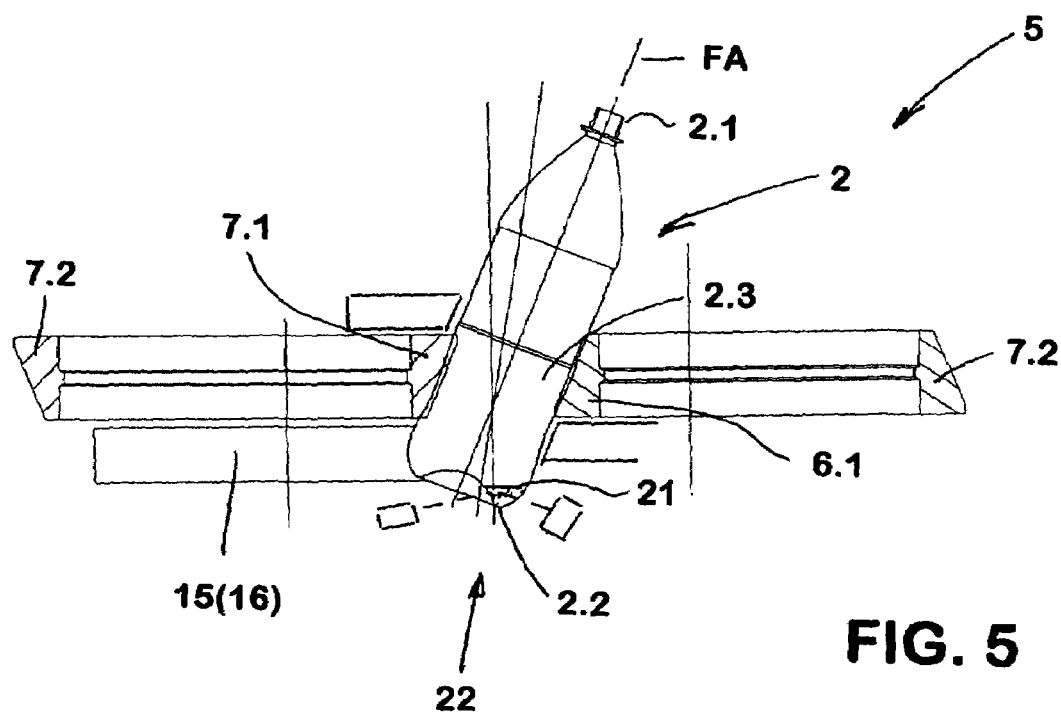
Figure 6:
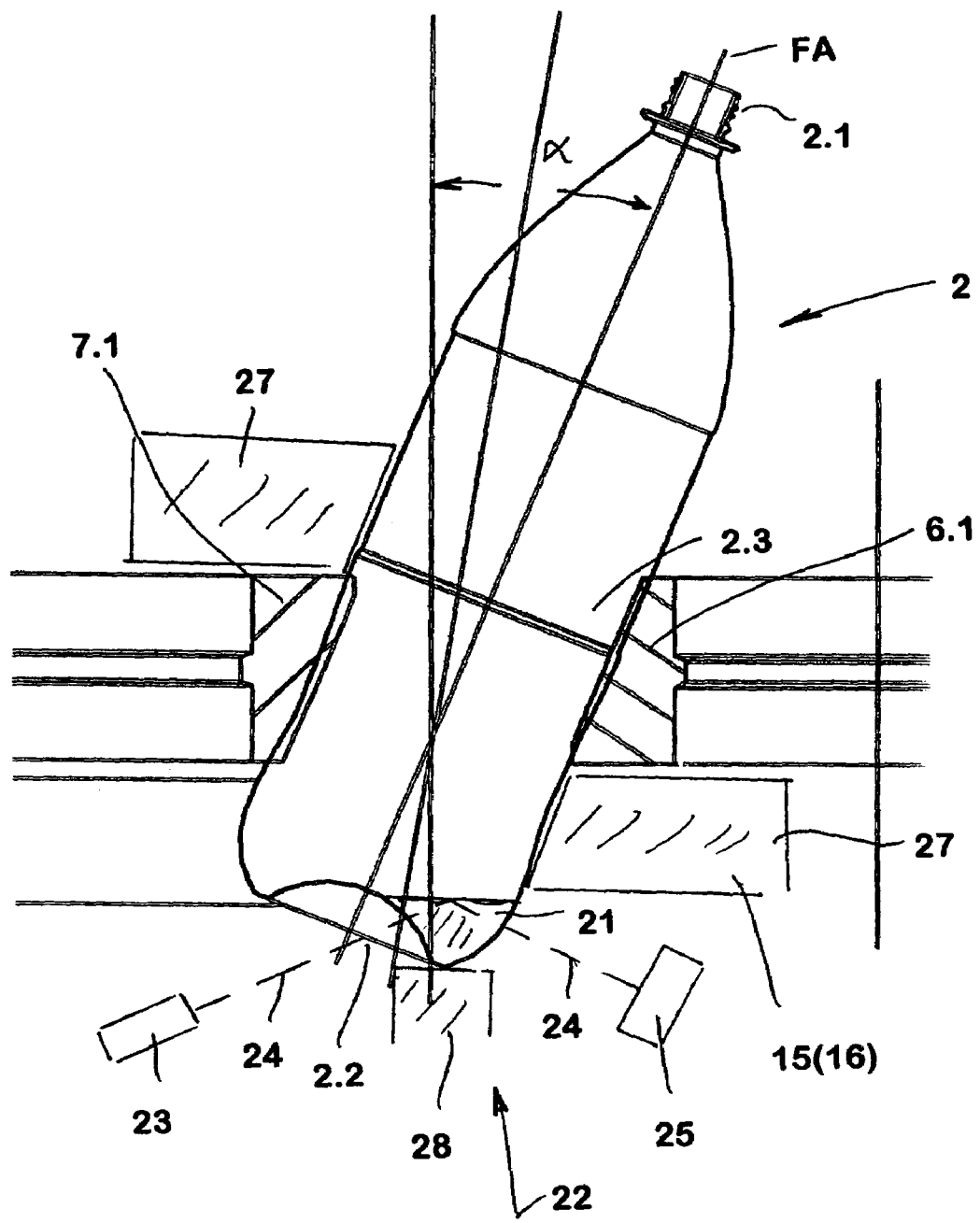
FIG. 6 is an enlarged drawing showing a detail of FIG. 5 in the vicinity of an inspection module.

The inspection of the inclined bottles 2 takes place in the middle area 8.3 of the conveyor line 8. For this purpose, the bottles 2 are filled with a precisely measured quantity of fluid 21 (e.g. sterile or clean water), which as a result of the inclined position of the respective bottles flows into a peripheral area of the bottom, as illustrated in FIGS. 5 and 6. By means of an inspection module 22, which is installed so that it is stationary, for example in the middle of the segment 8.3, each inclined bottle 2 that is moved past it and the fluid introduced into the respective bottle is tested or analyzed optoelectrically, and in at least one possible embodiment by a spectral analysis. For this purpose, the inspection module 22 in the illustrated exemplary embodiment comprises a light source 23 which emits a directional light beam 24, and a light detector 25 which supplies a sensor signal that is a function of the intensity and/or the spectral composition of the light beam 24 that strikes it.

The liquid 21, which in at least one possible embodiment is sterile water, is precisely measured out into each bottle 2 in a station 26 that is located upstream of the container inlet 8.1 in the transport direction A, specifically so that any foreign matter or foreign objects are carried off by the liquid 21 and/or dissolved in it, and so that the optoelectrical analysis or spectral analysis of the liquid 21 performed by the inspection module 21 can detect the presence or absence of foreign matter, foreign objects etc. in the respective bottle 2.

As illustrated in FIGS. 5 and 6, the light source 23 is located on one side of the conveyor line, namely on the side of the conveyor line 8 formed by the conveyor belt 7, so that the light beam 24 is directed to the concavely curved bottom segment in the vicinity of the edge of the bottom, and specifically in the illustrated exemplary embodiment so that the light beam 24 that enters the liquid 21 is reflected by total reflection on the surface of the liquid 21 to the light detector 24 that is located on the other side of the conveyor line 8. The total reflection is achieved by choosing an appropriate angle between the light beam 24 and the upper surface of the liquid 21.

One of the several advantages of the inclined position of the bottles 2 is that all of the foreign objects, foreign matter or similar impurities that may be present in bottle may be concentrated in a relatively small quantity of liquid 21 and a highly reliable inspection of the bottles 2 is thereby possible.

In at least one possible embodiment, the liquid 21 is swirled into the bottles or containers to cause the liquid 21 to travel across at least a substantial portion of the interior surface of the bottles. In this manner at least a substantial amount of the foreign matter, if any, on the interior surface or in the bottle will be collected by the liquid 21 prior to the settling of the liquid 21 at the bottom of the bottles. As discussed above, additional rotation of the bottles could be effected by differing the speeds of the conveyors 6 and 7, which could possibly assist in or cause the swirling movement of the liquid 21 in the bottles to further improve the gathering of debris and foreign matter in the bottles, if any.

To essentially guarantee a virtually unambiguous, reproducible inclined position of the bottles 2 as they pass the inspection module 22, additional guides are provided as indicated at 27 and 28 in FIG. 5, with which a specified angular position can be accurately achieved or promoted for each bottle 2 as it passes the inspection module 22.

Figure 7:
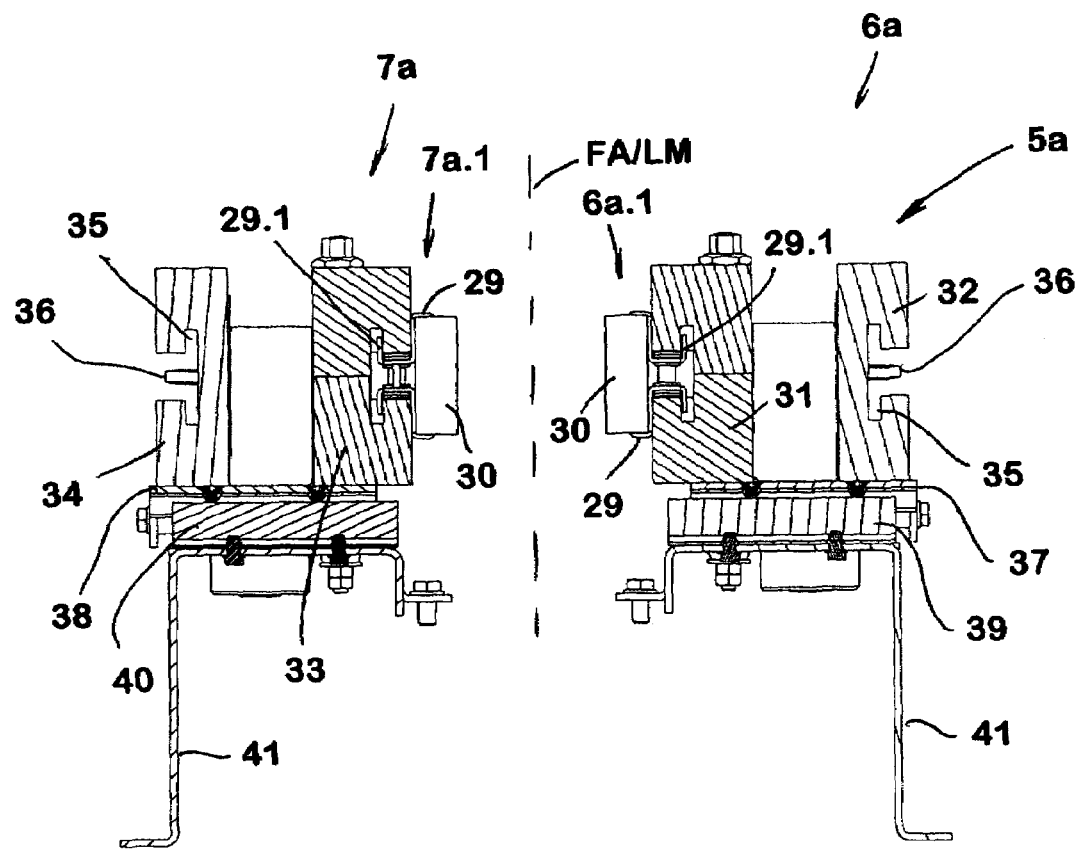
FIGS. 7 and 8 are sectional drawings through the conveyor element in an additional embodiment of the present application.
Figure 8:
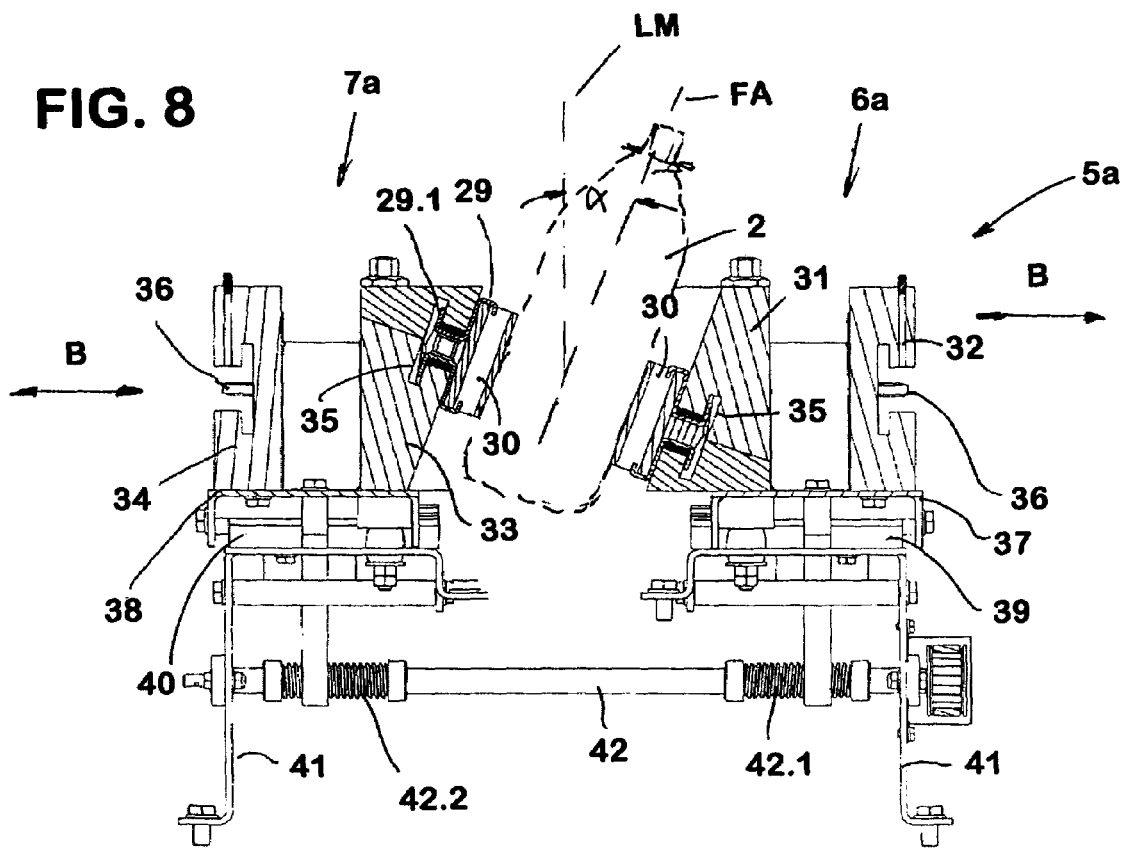

FIGS. 7 and 8 show in cross section a conveyor element 5a that corresponds to the conveyor element 5, the conveyor belts 6a and 7a of which, corresponding to the conveyor belts 6 and 7, are each formed by an endless, circulating driven chain that has a plurality of chain links 29. Each chain link 29 is provided with an elastic clamping jaw 30, so that the bottles 2 are held by clamping on their bottle shell 2.3 for the transport along the conveyor line 8a formed by the conveyor element 5a between the clamping jaws 30 of the conveyor belts 6a and 7a and of the conveyor belt lengths 6a.1 and 7a.1. The conveyor belts 6a and 7a and the chains that form these conveyor belts are in turn driven so that the conveyor belt lengths 6a.1 and 7a.1 that form the conveyor line 8a move in the same direction and at the same speed in the transport direction. The chain links 29 of the conveyor belts 6a and 7a are each guided positively with segments 29.1 in guide slots 35 of guides, and specifically the chain links 29 of the conveyor belt length 6a.1 that forms the conveyor line 8a on the guide 31, the chain links 29 of the outboard conveyor belt length 6a.2 on the guide 32, the chain links 29 of the conveyor belt length 7a.1 that forms the conveyor line 8a on the guide 33 and the chain links 29 of the outboard conveyor belt length 7a.2 on the guide 34.

FIG. 7 thereby shows a cross section of the conveyor element 5a at the container inlet or at the container outlet. FIG. 8 shows a cross section of the conveyor element 5a in an area between the container inlet and the container outlet, which corresponds, for example, to the area 8.3 of the conveyor element 5.

The guides 31 and 32 and 33 and 34 as well as the associated guide pulleys and sprocket wheels that are indicated as 36 in FIGS. 7 and 8 are each provided on slides 37 and 38, respectively, which can be adjusted in the horizontal direction perpendicular to the transport direction, so that it becomes possible to adjust the conveyor element 5a to bottles 2 of a different diameter, as is also indicated by the double arrow B. The slides 37 and 38 are guided on guides 39 and 40 respectively on a frame 41. By means of a spindle 42 with opposite threads 42.1 and 42.2, the two slides 37 and 38 and the conveyor belts 6a and 7a provided on them can be adjusted, with all the associated functional elements, thereby making it possible to adjust to the respective bottle diameter symmetrically to a vertical longitudinal center plane LM that encloses the transport direction.

As seen from a comparison of FIGS. 7 and 8, one particular feature of the conveyor element 5a is that the pivoting of the bottles 2 during the transport is achieved by a corresponding profile of the inner guides 31 and 33 and of their guide planes, and specifically as a result of the fact that the guide plane of these guides at the container inlet and at the container outlet is oriented as shown in FIG. 7 in the vertical direction and again encloses the angle α with the vertical between the container inlet and the container outlet and where the pivoting of the bottles 2 takes place (FIG. 8).

The chain links 29 and all the guides 31-34 are realized so that the conveyor belts 6a and 7a and their chain links are forcibly guided in three dimensional space in the guides. For this purpose, as described above, the chain links 29 are positively locked in a form-fitting connection with the segments 29.1 in the guide slots 35, which together with the outside surface of the respective guide define the guide plane along which the conveyor belts 6a and 7a and their chain links are moved.

Figure 9:
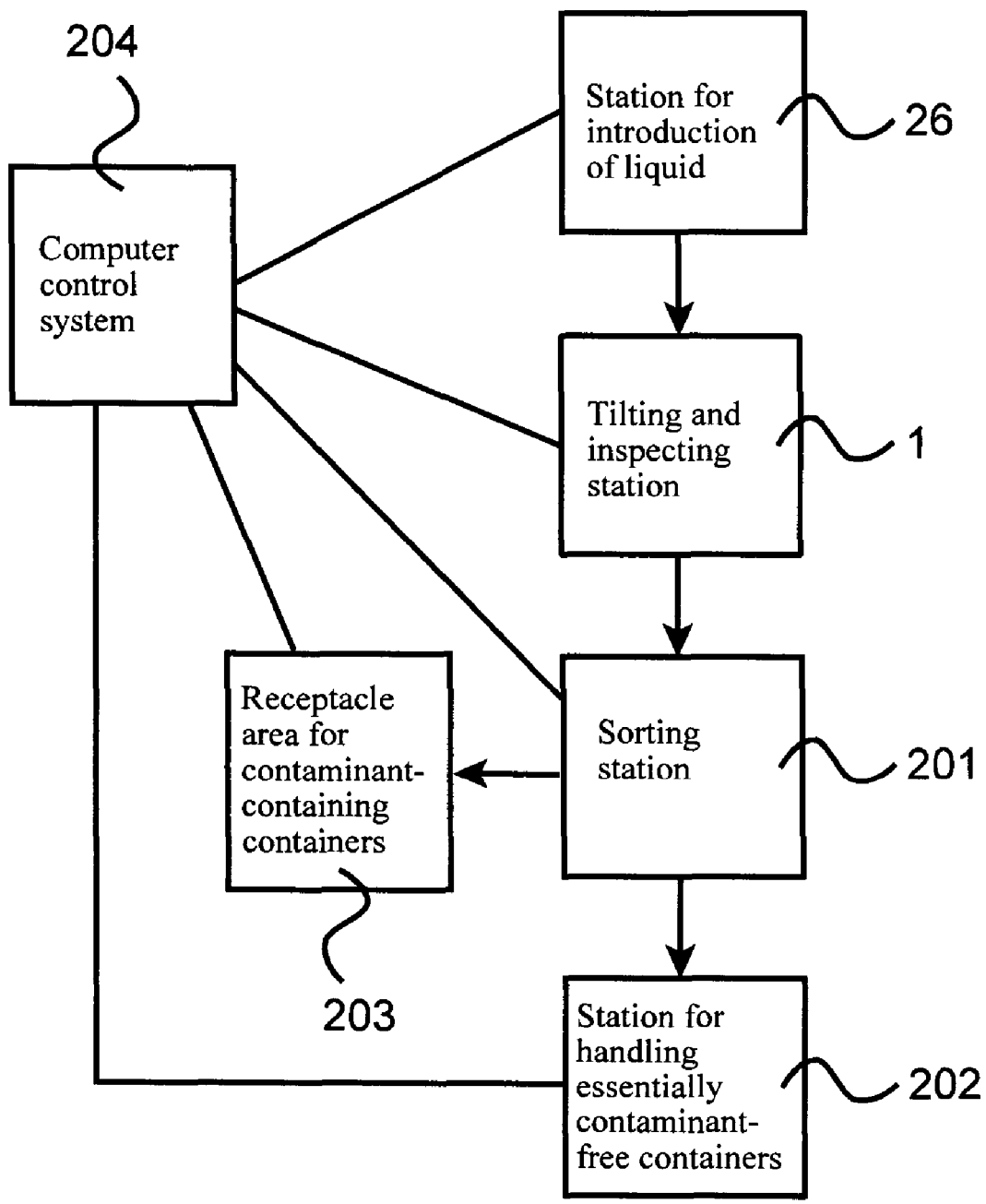
FIG. 9 shows a block diagram of at least one possible embodiment of a beverage bottling plant.

FIG. 9 shows a block diagram of at least one possible embodiment of a beverage bottling plant. In FIG. 9, an amount of liquid, such as sterile water, is dispensed into each bottle in station 26. Station 26, in at least one possible embodiment, comprises a device or arrangement for swirling the liquid into the bottles such that the liquid travels around and on a substantial portion of the inner surface of the bottles before settling by gravity in the bottom of the bottles to permit inspection of the liquid. After traveling through the station 26, the bottles enter the device 1 and are tilted by the conveyors therein, and the liquid is inspected by an inspection device for the presence of contaminants of sufficient quantity to contaminate a beverage that will be filled into the bottle. The inspection data is sent to the computer control system 204, while the bottles travel to a sorting station or machine 201. Based on the inspection data obtained by the computer control system 204, the sorting machine 201 either permits bottles considered to be sufficiently "clean," that is, sufficiently free from contaminants, to continue on into another station or machine 202 of the beverage bottling plant, or diverts or removes bottles considered to be "dirty," that is, containing a quantity of contaminants sufficient to contaminate the particular beverage to be filled in the bottle, to a receptacle area or machine or system 203. The "dirty" bottles can then be handled as desired, such as by disposal or further cleaning or recycling of the bottle material. In at least one possible embodiment, the control system 204 can be programmed to adjust the what is the acceptable, or unacceptable, level or threshold of quantity of contaminants for a particular beverage. In this manner, if a first beverage is more tolerant of contaminants than a second, different beverage being bottled in the same bottling plant, the level of acceptable contaminants can be adjusted to permit a greater or lesser number of bottles to be accepted for filling with the first beverage than would be accepted for the second beverage.

At least one possible embodiment of the present application has been explained above on the basis of exemplary embodiments. It goes without saying that numerous modifications and variants can be introduced without thereby going beyond the teaching of the present application.

In a method for the inspection of bottles or similar containers that are made of a translucent material, containers are moved in an inclined position past at least one inspection module or past at least one inspection station for an optical inspection.

At least one possible embodiment of the present application relates to a method and device for inspecting bottles or similar containers that are made of a translucent material, in which the containers are moved on a conveyor line in a transport direction past at least one inspection station, with a conveyor element with at least two conveyor belts that are driven in circulation and each form a closed loop, each of which forms with at least one conveyor belt length a conveyor line on which the containers are moved between the conveyor belt lengths held in a clamped seat in a transport direction.

One feature or aspect of an embodiment is believed at the time of the filing of this patent application to possibly reside broadly in a method for the inspection of bottles or similar containers 2 that are made of a translucent material, in which the containers 2 are moved on a conveyor line 8, 8a in a transport direction A past at least one inspection station 22, characterized in that the containers 2, which are fed to the machine standing in the upright position, are pivoted during the transport on the conveyor line 8, 8a and are moved past the at least one inspection module 22 in the pivoted position.

Another feature or aspect of an embodiment is believed at the time of the filing of this patent application to possibly reside broadly in the method, characterized in that the containers 2 are pivoted during transport on the conveyor line 8, 8a with their container axis FA in a plane perpendicular to the transport direction A for the inspection.

Yet another feature or aspect of an embodiment is believed at the time of the filing of this patent application to possibly reside broadly in the method, characterized in that the inspection of the containers 2 at the at least one inspection station 22 is performed optoelectrically using at least one light source 23 and at least one optoelectric sensor element, for example a light detector 25 or a camera system.

Still another feature or aspect of an embodiment is believed at the time of the filing of this patent application to possibly reside broadly in the method, characterized in that during the inspection the containers 2 are located with the area of the container to be inspected in the light path between the at least one light source 23 and the at least one optoelectric sensor element 25.

A further feature or aspect of an embodiment is believed at the time of the filing of this patent application to possibly reside broadly in the method, characterized in that the area of the container to be inspected is a bottom area, preferably a bottom area that is adjacent to a peripheral wall of the container.

Another feature or aspect of an embodiment is believed at the time of the filing of this patent application to possibly reside broadly in the method, characterized in that for containers 2 with a concavely curved container bottom 2.2 on the underside of the container, the light beam 24 of the at least one light source 23 is directed onto the concave bottom area of the containers 2 so that the light beam that penetrates the container 2 strikes the sensor element 25 that is located laterally with respect to the container 2.

Yet another feature or aspect of an embodiment is believed at the time of the filing of this patent application to possibly reside broadly in the method, characterized in that the inspection is performed with empty containers.

Still another feature or aspect of an embodiment is believed at the time of the filing of this patent application to possibly reside broadly in the method, characterized in that the inspection is performed with at least partly filled containers.

A further feature or aspect of an embodiment is believed at the time of the filing of this patent application to possibly reside broadly in the method, characterized in that, for the inspection, the containers 2 are each filled with a precisely measured quantity of liquid such as sterile water, for example.

Another feature or aspect of an embodiment is believed at the time of the filing of this patent application to possibly reside broadly in the method, characterized in that the light beam 24 from the at least one light source 23 is reflected by total reflection on the surface of the liquid 21 to the sensor element 25.

Yet another feature or aspect of an embodiment is believed at the time of the filing of this patent application to possibly reside broadly in the method, characterized in that a signal that corresponds to the condition of the respective container 2 is produced from the brightness and/or the spectrum of the light that strikes the sensor element 25.

Still another feature or aspect of an embodiment is believed at the time of the filing of this patent application to possibly reside broadly in the method, characterized in that, after the inspection and during the transport on the conveyor line 8, 8a, the containers 2 are returned to their upright position.

A further feature or aspect of an embodiment is believed at the time of the filing of this patent application to possibly reside broadly in the method, characterized in that the containers 2 are pivoted with their container axis FA by an angle α that is significantly less than 45°, for example by an angle of approximately 20°-25°.

Another feature or aspect of an embodiment is believed at the time of the filing of this patent application to possibly reside broadly in the method, characterized in that the containers (2) are made of glass or a translucent or transparent plastic, such as PET for example.

Yet another feature or aspect of an embodiment is believed at the time of the filing of this patent application to possibly reside broadly in a device, for the inspection of bottles or similar containers 2 that are made of a translucent material, with a conveyor element 5 with at least two conveyor belts 6, 7; 6a, 7a that are driven in circulation and each form a closed loop, each of which forms with at least one conveyor belt length 6.1, 7.1; 6a.1, 7a.1 a conveyor line 8, 8a on which the containers 2 are moved between the conveyor belt lengths 6.1, 7.1; 6a.1, 7a.1 held in a clamped seat in a transport direction A, characterized by means on the conveyor line 8, 8a to pivot the containers 2 that are fed in the upright position to a container inlet 8.1 of the conveyor line 8, 8a and removed at a container outlet 8.2 of the conveyor line 8, 8a in the upright position, at least once between the container inlet 8.1 and the container outlet 8.2 in the plane perpendicular to the transport direction A.

Still another feature or aspect of an embodiment is believed at the time of the filing of this patent application to possibly reside broadly in the device, characterized in that the means for the pivoting of the containers 2 are formed by the fact that the conveyor belts 6, 7 on the outside of their loops form inclined container stop or clamping surfaces corresponding to the pivoting angle of the containers 2, and that in the vicinity of the container inlet 8.1 and/or of the container outlet 8.2 there is at least one additional container support element 15, 16 that supports the containers 2 clamped between the conveyor belts 6, 7 during pivoting from the upright container position into the pivoted position and/or from the pivoted position into the upright position.

A further feature or aspect of an embodiment is believed at the time of the filing of this patent application to possibly reside broadly in the device, characterized in that the at least one container support element is located on one of the two conveyor belts 6, 7.

Another feature or aspect of an embodiment is believed at the time of the filing of this patent application to possibly reside broadly in the device, characterized in that the at least one container support element 15, 16 is formed by at least one additional, driven, endless circulating auxiliary or support belt 15, 16.

Yet another feature or aspect of an embodiment is believed at the time of the filing of this patent application to possibly reside broadly in the device, characterized in that the at least one auxiliary or support belt 15, 16 is driven in the same direction of rotation as the conveyor belts 6, 7 and at the same speed as the conveyor belts 6, 7.

Still another feature or aspect of an embodiment is believed at the time of the filing of this patent application to possibly reside broadly in the device, characterized in that the conveyor belts 6a, 7a are pivoted in a guide manner on guides 31-34 so that the containers 2 clamped between the conveyor belts 6a, 7a are pivoted at least once between the container inlet and the container outlet.

A further feature or aspect of an embodiment is believed at the time of the filing of this patent application to possibly reside broadly in the device, characterized in that the orientation of the guide planes of the guides 31, 33 for the conveyor belt lengths 6a.1, 7a.1 that form the conveyor line change at least once between the container inlet and the container outlet from a vertical orientation into an orientation that is inclined with respect to the vertical and back into the vertical orientation.

Another feature or aspect of an embodiment is believed at the time of the filing of this patent application to possibly reside broadly in the device, characterized in that the orientations of the guide planes of the guides 31, 33 for the conveyor belt lengths 6a.1, 7a.1 that form the conveyor line 81 change to the same degree along this conveyor line 8a.

Yet another feature or aspect of an embodiment is believed at the time of the filing of this patent application to possibly reside broadly in the device, characterized in that the conveyor belts 6a, 7a are chains with clamping jaws 30 provided on chain links 29.

Still another feature or aspect of an embodiment is believed at the time of the filing of this patent application to possibly reside broadly in a beverage bottling plant for filling beverage bottles with liquid beverage material, said beverage bottling plant comprising: a beverage bottle handling machine being configured and disposed to handle beverage bottles; a first conveyor arrangement being configured and disposed to convey beverage bottles to said beverage bottle handling machine; a beverage bottle filling machine being configured and disposed to fill beverage bottles with liquid beverage material; a second conveyor arrangement being configured and disposed to convey at least a portion of beverage bottles handled by said beverage bottle handling machine to said beverage bottle filling machine; a beverage bottle closing machine being configured and disposed to close tops of filled beverage bottles; a third conveyor arrangement being configured and disposed to convey filled beverage bottles to said beverage bottle closing machine; a beverage bottle packing machine being configured and disposed to pack closed, filled beverage bottles; a fourth conveyor arrangement being configured and disposed to convey closed, filled beverage bottles to said beverage bottle packing machine; a central control system being operatively connected to each of said machines to monitor and control the operation thereof; said beverage bottle filling machine comprising: a rotor; a rotatable vertical machine column; said rotor being connected to said vertical machine column to permit rotation of said rotor about said vertical machine column; a plurality of beverage bottle filling elements for filling beverage bottles with liquid beverage material being disposed on the periphery of said rotor; each of said plurality of beverage bottle filling elements comprising a container carrier being configured and disposed to receive and hold beverage bottles to be filled; each of said plurality of beverage bottle filling elements being configured and disposed to dispense liquid beverage material into beverage bottles to be filled; at least one liquid reservoir being configured to hold a supply of liquid beverage material; at least one supply line being configured and disposed to connect said at least one liquid reservoir to said beverage bottle filling machine to supply liquid beverage material to said beverage bottle filling machine; a first star wheel structure being configured and disposed to move beverage bottles into said beverage bottle filling machine; and a second star wheel structure being configured and disposed to move beverage bottles out of said beverage bottle filling machine; said beverage bottle closing machine comprising: a rotor; a rotatable vertical machine column; said rotor being connected to said vertical machine column to permit rotation of said rotor about said vertical machine column; a plurality of closing devices being disposed on the periphery of said rotor; each of said plurality of closing devices being configured and disposed to place closures on filled beverage bottles; each of said plurality of closing devices comprising a container carrier being configured and disposed to receive and hold filled beverage bottles; a first star wheel structure being configured and disposed to move filled beverage bottles into said beverage bottle closing machine; and a second star wheel structure being configured and disposed to move filled, closed beverage bottles out of said beverage bottle closing machine; said beverage bottle packing machine comprising: a sorting arrangement being configured and disposed to sort and group beverage bottles into groups; and a packaging arrangement being configured and disposed to package the groups of beverage bottles; said beverage bottle handling machine comprising: a liquid dispensing device being configured and disposed to dispense an amount of clean water into beverage bottles to rinse observable, liquid-beverage contaminants from a substantial portion of the interior surface of the beverage bottles and gather the contaminants in the amount of clean water at the bottom of the beverage bottles; a conveyor device comprising a first conveyor belt and a second conveyor belt, each being in the form of closed loops; said first conveyor belt and said second conveyor belt being disposed adjacent one another to define a beverage bottle transport path there between; said first conveyor belt and said second conveyor belt being configured and disposed to together hold and move beverage bottles there between in a transport direction along the beverage bottle transport path; said conveyor device comprising a beverage bottle inlet area and a beverage bottle outlet area being disposed opposite ends of said conveyor device; said conveyor device being configured and disposed to receive beverage bottles in their upright position at the beverage bottle inlet area upon dispensing of clean water into the beverage bottles by said liquid dispensing device; said conveyor device being configured and disposed to transport the beverage bottles out of the conveyor device in their upright position at the beverage bottle outlet area; said conveyor belts being configured and disposed to temporarily tilt beverage bottles being held and moved there between from their upright position to a tilted position in a plane perpendicular to the transport direction in between said beverage bottle inlet and outlet areas to gather the water in the beverage bottles in a bottom portion of the beverage bottles; an observation device being configured and disposed to observe the amount of water in tilted beverage bottles being held and moved by said conveyor belts to discern the presence of contaminants in a sufficient quantity to contaminate liquid beverage material in a filled beverage bottle; said observation device being configured and disposed to send beverage bottle observation information to said control system; a separating device being configured and disposed to receive observed beverage bottles from said conveyor device and separate beverage bottles having a quantity of contaminants sufficient to contaminate liquid beverage material from beverage bottles being sufficiently free of contaminants; said separating device being configured and disposed to receive beverage bottle separation information from said control system based on the observation information received by said control system from said observation device; said separating device comprising a first separating conveyor and a second separating conveyor; said first separating conveyor being configured and disposed to convey beverage bottles being sufficiently free of contaminants out of said beverage bottle handling machine for further handling in said beverage bottling plant; and said second separating conveyor being configured and disposed to convey beverage bottles being sufficiently contaminated out of said beverage bottle handling machine for disposal.

A further feature or aspect of an embodiment is believed at the time of the filing of this patent application to possibly reside broadly in a method of operating the beverage bottling plant, said method comprising the steps of: moving beverage bottles to said beverage bottle handling station; dispensing with said liquid dispensing device an amount of clean water into beverage bottles and rinsing observable, liquid-beverage contaminants from a substantial portion of the interior surface of the beverage bottles and gathering the contaminants in the amount of clean water at the bottom of the beverage bottles; receiving beverage bottles in their upright position at said beverage bottle inlet area into said conveyor device from said liquid dispensing device; holding and moving beverage bottles with said conveyor belts; tilting beverage bottles with said conveyor belts to a position in a plane perpendicular to the transport direction of the beverage bottles during the movement thereof along said beverage bottle transport path and gathering the water in a bottom portion of the beverage bottles; observing with said observation device the amount of water in the tilted beverage bottles and discerning the presence of contaminants in a sufficient quantity to contaminate liquid beverage material in a filled beverage bottle; sending beverage bottle observation information from said observation device to said control system; tilting beverage bottles with said conveyor belts back to their upright position at said beverage bottle outlet area; moving beverage bottles in their upright position out of said conveyor device and into said separating device; receiving with said separation device observation information from said control system and separating beverage bottles having a quantity of contaminants sufficient to contaminate liquid beverage material from beverage bottles being sufficiently free of contaminants; moving beverage bottles being sufficiently free of contaminants out of said beverage bottle handling machine for further handling in said beverage bottling plant; moving beverage bottles being sufficiently contaminated out of said beverage bottle handling machine for disposal; moving beverage bottles being sufficiently free of contaminants to said filling machine and filling the beverage bottles with a liquid beverage material in said filling machine; moving filled beverage bottles to said closing machine and closing filled beverage bottles with a closure in said closing machine; and moving filled, closed beverage bottles to said packing machine and sorting, grouping, and packaging filled, closed beverage bottles in packages.

Another feature or aspect of an embodiment is believed at the time of the filing of this patent application to possibly reside broadly in a method of operating a beverage bottling plant, said method comprising the steps of: moving beverage bottles to a beverage bottle handling station; dispensing with a liquid dispensing device an amount of liquid into beverage bottles and rinsing observable, liquid-beverage contaminants from a substantial portion of the interior surface of the beverage bottles and gathering the contaminants in the amount of liquid at the bottom of the beverage bottles; receiving beverage bottles in their upright position at a beverage bottle inlet area into a conveyor device from said liquid dispensing device; holding and moving beverage bottles in said conveyor device; tilting beverage bottles during the movement thereof in said conveyor device and gathering the liquid in a bottom portion of the beverage bottles; observing with an observation device the liquid in the tilted beverage bottles and discerning the presence of contaminants in the liquid in a sufficient quantity to contaminate liquid beverage material in a filled beverage bottle; sending beverage bottle observation information from said observation device to a control system; moving beverage bottles out of said conveyor device and into a separating device; receiving with said separation device observation information from said control system and separating beverage bottles having a quantity of contaminants sufficient to contaminate liquid beverage material from beverage bottles being sufficiently free of contaminants; moving beverage bottles being sufficiently free of contaminants out of said beverage bottle handling machine to a first location for further handling in said beverage bottling plant; moving beverage bottles being sufficiently contaminated out of said beverage bottle handling machine to a second location other than said first location; moving beverage bottles being sufficiently free of contaminants to a filling machine and filling the beverage bottles with a liquid beverage material in said filling machine; moving filled beverage bottles to a closing machine and closing filled beverage bottles with a closure in said closing machine; and moving filled, closed beverage bottles to a packing machine and sorting, grouping, and packaging filled, closed beverage bottles in packages.

Some examples of a swirl-inducing device for causing swirling of liquid in a filling machine which may possibly be used in at least one possible embodiment may possibly be found in U.S. Pat. No. 5,501,253, entitled "Apparatus for filling vessels with liquid;" U.S. Pat. No. 5,190,084, entitled "Filling element for filling machines for dispensing liquid;" and U.S. Pat. No. 4,757,847, entitled "Filling machine filling element having no filling tube."

The components disclosed in the various publications, disclosed or incorporated by reference herein, may possibly be used in possible embodiments of the present application, as well as equivalents thereof.

Some examples of bottling systems and components thereof, which may be used or adapted for use in at least one possible embodiment of the present application may be found in the following U.S. Patents assigned to the Assignee herein, namely: U.S. Pat. No. 4,911,285; No. 4,944,830; No. 4,950,350; No. 4,976,803; No. 4,981,547; No. 5,004,518; No. 5,017,261; No. 5,062,917; No. 5,062,918; No. 5,075,123; No. 5,078,826; No. 5,087,317; No. 5,110,402; No. 5,129,984; No. 5,167,755; No. 5,174,851; No. 5,185,053; No. 5,217,538; No. 5,227,005; No. 5,413,153; No. 5,558,138; No. 5,634,500; No. 5,713,403; No. 6,276,113; No. 6,213,169; No. 6,189,578; No. 6,192,946; No. 6,374,575; No. 6,365,054; No. 6,619,016; No. 6,474,368; No. 6,494,238; No. 6,470,922; and No. 6,463,964.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

Some examples of filling machines that utilize electronic control devices to control various portions of a filling or bottling process and that may possibly be utilized or possibly adapted for use in at least one possible embodiment of the present application may possibly be found in the following U.S. Pat. No. 4,821,921 issued to Cartwright et al. on Apr. 18, 1989; U.S. Pat. No. 5,056,511 issued to Ronge on Oct. 15, 1991; U.S. Pat. No. 5,273,082 issued to Paasche et al. on Dec. 28, 1993; and U.S. Pat. No. 5,301,488 issued to Ruhl et al. on Apr. 12, 1994.

The appended drawings in their entirety, including all dimensions, proportions and/or shapes in at least one embodiment of the present application, are accurate and are hereby included by reference into this specification.

Some examples of inspection devices and/or spectral analyzers, and components thereof, that may possibly be utilized or possibly adapted for use in at least one possible embodiment of the present application may possibly be found in the following U.S. patents: U.S. Pat. No. 6,424,416 issued to Gross et al. on Jul. 23, 2002; U.S. Pat. No. 6,040,906 issued to Harhay on Mar. 21, 2000; U.S. Pat. No. 6,281,499 issued to Kobayashi, et al. on Aug. 28, 2001; U.S. Pat. No. 5,319,437 issued to Van Aken, et al. on Jun. 7, 1994; U.S. Pat. No. 6,120,166 issued to Price on Sep. 19, 2000; U.S. Pat. No. 5,428,222 issued to Alexay on Jun. 27, 1995; and U.S. Pat. No. 6,937,339 issued to Yamazaki on Aug. 30, 2005.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

Some examples of apparatus and methods of sterilizing or cleaning containers that may possibly be utilized or possibly adapted for use in at least one possible embodiment of the present application may possibly be found in the following U.S. Patents: U.S. Pat. No. 5,092,356 issued to Grot on Mar. 3, 1992; U.S. Pat. No. 5,320,144 issued to Ahlers on Jun. 14, 1994; U.S. Pat. No. 5,533,552 issued to Ahlers on Jul. 9, 1996; U.S. Pat. No. 5,558,135 issued to Kronseder et al. on Sep. 24, 1996; and U.S. Pat. No. 5,896,899 issued to Schlitz on Apr. 27, 1999.

All, or substantially all, of the components and methods of the various embodiments may be used with at least one embodiment or all of the embodiments, if more than one embodiment is described herein.

Some examples of bottling and container handling systems and components thereof which may possibly be utilized or adapted for use in at least one possible embodiment, may possibly be found in the following U.S. Patents: U.S. Pat. No. 6,484,477, entitled "Capping Machine for Capping and Closing Containers, and a Method for Closing Containers;" U.S. Pat. No. 6,474,368, entitled "Beverage Container Filling Machine, and Method for Filling Containers with a Liquid Filling Material in a Beverage Container Filling Machine;" U.S. Pat. No. 6,494,238, entitled "A Plant for Filling Beverage into Beverage Bottles Other Beverage Containers Having Apparatus for Replacing Remaining Air Volume in Filled Beverage Bottles or Other Beverage Containers;" U.S. Pat. No. 6,470,922, entitled "Apparatus for the Recovery of an Inert Gas;" U.S. Pat. No. 6,463,964, entitled "Method of Operating a Plant for Filling Bottles, Cans or the like Beverage Containers with a Beverage, and a Beverage Container Filling Machine;" U.S. Pat. No. 6,834,473, entitled "Bottling Plant and Method of Operating a Bottling Plant and a Bottling Plant with Sections for Stabilizing the Bottled Product;" U.S. Pat. No. 6,484,762, entitled "A Filling System with Post-dripping Prevention;" U.S. Pat. No. 6,668,877, entitled "Filling System for Still Beverages;" U.S. Pat. No. 7,024,841, entitled "Labeling Machine with a Sleeve Mechanism for Preparing and Applying Cylindrical Labels onto Beverage Bottles and Other Beverage Containers in a Beverage Container Filling Plant;" U.S. Pat. No. 6,971,219 entitled "Beverage bottling plant for filling bottles with a liquid beverage filling material and a labelling station for labelling filled bottles and other containers;" U.S. Pat. No. 6,973,767, entitled "Beverage bottling plant and a conveyor arrangement for transporting packages;" U.S. Pat. No. 7,013,624, entitled "Beverage bottling plant for filling bottles with a liquid beverage filling material, a container filling plant container information adding station, such as, a labeling station, configured to add information to containers, such as, bottles and cans, and modules for labeling stations;" U.S. Pat. No. 7,108,025, entitled "Beverage Bottling Plant for Filling Bottles with a Liquid Beverage Filling Material, and a Container Filling Lifting Device for Pressing Containers to Container Filling Machines;" U.S. Pat. No. 7,062,894, entitled "Beverage Bottling Plant for Filling Bottles with a Liquid Beverage Filling Material, and a Container Filling Plant Container Information Adding Station, Such As, a Labeling Station Having a Sleeve Label Cutting Arrangement, Configured to Add Information to Containers, Such As, Bottles and Cans;" U.S. Pat. No. 7,010,900, entitled "Beverage Bottling Plant for Filling Bottles with a Liquid Beverage Filling Material, and a Cleaning Device for Cleaning Bottles in a Beverage Bottling Plant;" U.S. Pat. No. 6,918,417, entitled "A Beverage Bottling Plant for Filling Bottles with a Liquid Beverage Filling Material, and an Easily Cleaned Lifting Device in a Beverage Bottling Plant;" U.S. Pat. No. 7,065,938, entitled "A Beverage Bottling Plant for Filling Bottles with a Liquid Beverage Filling Material, and a Container Filling Plant Container Information Adding Station, Such As, a Labeling Station Having a Gripper Arrangement, Configured to Add Information to Containers, Such As, Bottles and Cans;" U.S. Pat. No. 6,901,720, entitled "A Beverage Bottling Plant for Filling Bottles with a Liquid Beverage Filling Material, and Apparatus for Attaching Carrying Grips to Containers with Filled Bottles;" and U.S. Pat. No. 7,121,062 "Beverage bottling plant for filling bottles with a liquid beverage filling material, having a container handling machine with interchangeable receptacles for the container mouth."

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

Some examples of bottling and container handling systems and components thereof which may possibly be utilized or adapted for use in at least one possible embodiment, may possibly be found in the following U.S. patent applications: Ser. No. 10/723,451, filed on Nov. 26, 2003, entitled "Beverage Bottling Plant for Filling Beverage Bottles or Other Beverage Containers with a Liquid Beverage Filling Material and Arrangement for Dividing and Separating of a Stream of Beverage Bottles or Other Beverage Containers;" Ser. No. 10/739,895, filed on Dec. 18, 2003, entitled "Method of Operating a Beverage Container Filling Plant with a Labeling Machine for Labeling Beverage Containers Such as Bottles and Cans, and a Beverage Container Filling Plant with a Labeling Machine for Labeling Beverage Containers Such as Bottles and Cans;" Ser. No. 10/865,240, filed on Jun. 10, 2004, Entitled "A Beverage Bottling Plant for Filling Bottles with a Liquid Beverage Filling Material, a Beverage Container Filling Machine, and a Beverage Container Closing Machine;" Ser. No. 10/883,591, filed on Jul. 1, 2004, entitled "A Beverage Bottling Plant for Filling Bottles with a Liquid Beverage Filling Material Having a Container Filling Plant Container Information Adding Station, Such As, a Labeling Station, Configured to Add Information to Containers, Such As, Bottles and Cans, and Modules for Labeling Stations and a Bottling Plant Having a Mobile Module Carrier;" Ser. No. 10/930,678, filed on Aug. 31, 2004, entitled "A Beverage Bottling Plant for Filling Bottles with a Liquid Beverage Filling Material, a Container Filling Plant Container Filling Machine, and a Filter Apparatus for Filtering a Liquid Beverage;" Ser. No. 10/931,817, filed on Sep. 1, 2004, entitled "A Beverage Bottling Plant for Filling Bottles with a Liquid Beverage Filling Material, Having an Apparatus for Exchanging Operating Units Disposed at Rotating Container Handling Machines;" Ser. No. 10/954,012, filed on Sep. 29, 2004, Ser. No. 10/952,706, Ser. No. 10/962,183, filed on Oct. 8, 2004, Ser. No. 10/967,016, filed on Oct. 15, 2004, Ser. No. 10/982,706, filed on Nov. 5, 2004, Ser. No. 10/982,694, Ser. No. 10/982,710, Ser. No. 10/984,677, filed on Nov. 9, 2004, Ser. No. 10/985,640, filed on Nov. 10, 2004, Ser. No. 11/004,663, filed on Dec. 3, 2004, Ser. No. 11/009,551, filed on Dec. 10, 2004, Ser. No. 11/012,859, filed on Dec. 15, 2004, Ser. No. 11/014,673, filed on Dec. 16, 2004, Ser. No. 11/016,364, filed on Dec. 17, 2004, and Ser. No. 11/016,363.

All of the patents, patent applications and publications recited herein, and in the Declaration attached hereto, are hereby incorporated by reference as if set forth in their entirety herein.

Some examples of cameras or the like optical monitoring apparatus that may possibly be utilized or possibly adapted for use in at least one possible embodiment of the present application may possibly be found in the following U.S. patents: U.S. Pat. No. 5,233,186 issued to Ringlien on Aug. 3, 1993; U.S. Pat. No. 5,243,400 issued to Ringlien on Sep. 7, 1993; U.S. Pat. No. 5,369,713 issued to Schwartz et al. on Nov. 29, 1994; U.S. Pat. No. 5,442,446 issued to Gerber et al. on Aug. 15, 1995; U.S. Pat. No. 5,661,295 issued to Buchmann et al. on Aug. 26, 1997; and U.S. Pat. No. 5,898,169 issued to Nodbryhn on Apr. 27, 1999.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, published patent applications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, published patent applications and other documents either incorporated by reference or not incorporated by reference.

The corresponding foreign and international patent publication applications, namely, Federal Republic of Germany Patent Application No. 10 2006 002 633.0, filed on Jan. 19, 2006, having inventor Gyula VARHANIOVSKY, and DE-OS 10 2006 002 633.0 and DE-PS 10 2006 002 633.0, are hereby incorporated by reference as if set forth in their entirety herein for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications and publications, are hereby incorporated by reference as if set forth in their entirety herein.

All of the references and documents, cited in any of the documents cited herein, are hereby incorporated by reference as if set forth in their entirety herein. All of the documents cited herein, referred to in the immediately preceding sentence, include all of the patents, patent applications and publications cited anywhere in the present application.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications and publications may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the present application described herein above in the context of the preferred embodiments are not to be taken as limiting the embodiments of the present application to all of the provided details thereof, since modifications and variations thereof may be made without departing from the spirit and scope of the embodiments of the present application.

AT LEAST PARTIAL NOMENCLATURE

1 Device
2 Bottle
2.1 Bottle mouth
2.2 Bottle bottom
2.3 Bottle shell
3.4 Conveyor
5, 5a Conveyor or conveyor element
6, 6a, 7, 7a Conveyor belt
6.1, 7.1 Conveyor belt length
8, 8a Conveyor line
9 Guide pulley
10 Driven pulley
11 Deflector or tensioning roller
12 Guide pulley
13 Driven pulley
14 Deflector or tensioning roller
15, 16 Support belt
15.1, 16.1 Support belt length
17 Guide pulley
18 Tensioning pulley
19 Guide pulley
20 Tensioning pulley
21 Test liquid
22 Inspection module
23 Light source
24 Light beam
25 Light detector
26 Station for the introduction of the test liquid 21
27, 28 Guide
29 Chain link
29.1 Chain link segment
30 Clamping jaws
31, 32, 33, 34 Guide
35 Guide slot
36 Sprocket wheel
37, 38 Slides
39, 40 Slide guide
41 Machine frame
42 Spindle
42.1, 42.2 Threaded segment
A Transport direction
B Adjustment of the width of the conveyor line 8 and 8a
LM Vertical longitudinal center plane
QM Vertical transverse center plane
α, β Angle

What is claimed is:

1. A method of operating a beverage bottling plant for filling beverage bottles with liquid beverage material, said beverage bottling plant comprising: a beverage bottle handling machine being configured and disposed to handle beverage bottles; a first conveyor arrangement being configured and disposed to convey beverage bottles to said beverage bottle handling machine; a beverage bottle filling machine being configured and disposed to fill beverage bottles with liquid beverage material; a second conveyor arrangement being configured and disposed to convey at least a portion of beverage bottles handled by said beverage bottle handling machine to said beverage bottle filling machine; a beverage bottle closing machine being configured and disposed to close tops of filled beverage bottles; a third conveyor arrangement being configured and disposed to convey filled beverage bottles to said beverage bottle closing machine; a beverage bottle packing machine being configured and disposed to pack closed, filled beverage bottles; a fourth conveyor arrangement being configured and disposed to convey closed, filled beverage bottles to said beverage bottle packing machine; a central control system being operatively connected to each of said machines to monitor and control the operation thereof; said beverage bottle filling machine comprising: a rotor; a rotatable vertical machine column; said rotor being connected to said vertical machine column to permit rotation of said rotor about said vertical machine column; a plurality of beverage bottle filling elements for filling beverage bottles with liquid beverage material being disposed on the periphery of said rotor; each of said plurality of beverage bottle filling elements comprising a container carrier being configured and disposed to receive and hold beverage bottles to be filled; each of said plurality of beverage bottle filling elements being configured and disposed to dispense liquid beverage material into beverage bottles to be filled; at least one liquid reservoir being configured to hold a supply of liquid beverage material; at least one supply line being configured and disposed to connect said at least one liquid reservoir to said beverage bottle filling machine to supply liquid beverage material to said beverage bottle filling machine; a first star wheel structure being configured and disposed to move beverage bottles into said beverage bottle filling machine; and a second star wheel structure being configured and disposed to move beverage bottles out of said beverage bottle filling machine; said beverage bottle closing machine comprising: a rotor; a rotatable vertical machine column; said rotor being connected to said vertical machine column to permit rotation of said rotor about said vertical machine column; a plurality of closing devices being disposed on the periphery of said rotor; each of said plurality of closing devices being configured and disposed to place closures on filled beverage bottles; each of said plurality of closing devices comprising a container carrier being configured and disposed to receive and hold filled beverage bottles; a first star wheel structure being configured and disposed to move filled beverage bottles into said beverage bottle closing machine; and a second star wheel structure being configured and disposed to move filled, closed beverage bottles out of said beverage bottle closing machine; said beverage bottle packing machine comprising: a sorting arrangement being configured and disposed to sort and group beverage bottles into groups; and a packaging arrangement being configured and disposed to package the groups of beverage bottles; said beverage bottle handling machine comprising: a liquid dispensing device being configured and disposed to dispense an amount of clean water into beverage bottles to rinse observable, liquid-beverage contaminants from a substantial portion of the interior surface of the beverage bottles and gather the contaminants in the amount of clean water at the bottom of the beverage bottles; a conveyor device comprising a first conveyor belt and a second conveyor belt, each being in the form of closed loops; said first conveyor belt and said second conveyor belt being disposed adjacent one another to define a beverage bottle transport path there between; said first conveyor belt and said second conveyor belt being configured and disposed to together hold and move beverage bottles there between in a transport direction along the beverage bottle transport path; said conveyor device comprising a beverage bottle inlet area and a beverage bottle outlet area being disposed opposite ends of said conveyor device; said conveyor device being configured and disposed to receive beverage bottles in their upright position at the beverage bottle inlet area upon dispensing of clean water into the beverage bottles by said liquid dispensing device; said conveyor device being configured and disposed to transport the beverage bottles out of the conveyor device in their upright position at the beverage bottle outlet area; said conveyor belts being configured and disposed to temporarily tilt beverage bottles being held and moved there between from their upright position to a tilted position in a plane perpendicular to the transport direction in between said beverage bottle inlet and outlet areas to gather the water in the beverage bottles in a bottom portion of the beverage bottles; an observation device being configured and disposed to observe the amount of water in tilted beverage bottles being held and moved by said conveyor belts to discern the presence of contaminants in a sufficient quantity to contaminate liquid beverage material in a filled beverage bottle; said observation device being configured and disposed to send beverage bottle observation information to said control system; a separating device being configured and disposed to receive observed beverage bottles from said conveyor device and separate beverage bottles having a quantity of contaminants sufficient to contaminate liquid beverage material from beverage bottles being sufficiently free of contaminants; said separating device being configured and disposed to receive beverage bottle separation information from said control system based on the observation information received by said control system from said observation device; said separating device comprising a first separating conveyor and a second separating conveyor; said first separating conveyor being configured and disposed to convey beverage bottles being sufficiently free of contaminants out of said beverage bottle handling machine for further handling in said beverage bottling plant; and said second separating conveyor being configured and disposed to convey beverage bottles being sufficiently contaminated out of said beverage bottle handling machine for disposal; said method comprising the steps of:

moving beverage bottles to said beverage bottle handling station;

dispensing with said liquid dispensing device an amount of clean water into beverage bottles and rinsing observable, liquid-beverage contaminants from a substantial portion of the interior surface of the beverage bottles and gathering the contaminants in the amount of clean water at the bottom of the beverage bottles;

receiving beverage bottles in their upright position at said beverage bottle inlet area into said conveyor device from said liquid dispensing device;

holding and moving beverage bottles with said conveyor belts;

tilting beverage bottles with said conveyor belts to a position in a plane perpendicular to the transport direction of the beverage bottles during the movement thereof along said beverage bottle transport path and gathering the water in a bottom portion of the beverage bottles;

observing with said observation device the water in the tilted beverage bottles and discerning the presence of contaminants in the water in a sufficient quantity to contaminate liquid beverage material in a filled beverage bottle;

sending beverage bottle observation information from said observation device to said control system;

tilting beverage bottles with said conveyor belts back to their upright position at said beverage bottle outlet area;

moving beverage bottles in their upright position out of said conveyor device and into said separating device;

receiving with said separation device observation information from said control system and separating beverage bottles having a quantity of contaminants sufficient to contaminate liquid beverage material from beverage bottles being sufficiently free of contaminants;

moving beverage bottles being sufficiently free of contaminants out of said beverage bottle handling machine for further handling in said beverage bottling plant;

moving beverage bottles being sufficiently contaminated out of said beverage bottle handling machine for disposal;

moving beverage bottles being sufficiently free of contaminants to said filling machine and filling the beverage bottles with a liquid beverage material in said filling machine;

moving filled beverage bottles to said closing machine and closing filled beverage bottles with a closure in said closing machine; and moving filled, closed beverage bottles to said packing machine and sorting, grouping, and packaging filled, closed beverage bottles in packages.

2. The method of operating a beverage bottling plant according to claim 1, wherein the observation of the beverage bottles is performed optoelectrically using at least one light source and at least one optoelectric sensor element comprising one of: a light detector or a camera system; and during the observation, the beverage bottles are located with the area of the beverage bottle to be inspected in the light path between the at least one light source and the at least one optoelectric sensor element; and the area of the beverage bottle to be inspected is a bottom area that is adjacent to a peripheral wall of the beverage bottle.

3. The method of operating a beverage bottling plant according to claim 2, wherein for beverage bottles with a concavely curved beverage bottle bottom on the underside of the beverage bottle, the light beam of the at least one light source is directed onto the concave bottom area of the beverage bottles so that the light beam that penetrates the beverage bottle strikes the sensor element that is located laterally with respect to the beverage bottle.

4. The method of operating a beverage bottling plant according to claim 3, wherein the light beam from the at least one light source is reflected by total reflection on the surface of the liquid to the sensor element; and a signal that corresponds to the condition of the respective beverage bottle is produced from at least one of: the brightness and the spectrum of the light that strikes the sensor element.

5. The method of operating a beverage bottling plant according to claim 4, wherein the beverage bottles are pivoted with their beverage bottle axis by an angle that is one of: substantially less than 45° and approximately 20°-25°; and the beverage bottles are made of one of: glass, a translucent or transparent plastic, and PET.

6. A beverage bottling plant for filling beverage bottles with liquid beverage material, said beverage bottling plant comprising:
- a beverage bottle handling machine being configured and disposed to handle beverage bottles;
- a first conveyor arrangement being configured and disposed to convey beverage bottles to said beverage bottle handling machine;
- a beverage bottle filling machine being configured and disposed to fill beverage bottles with liquid beverage material;
- a second conveyor arrangement being configured and disposed to convey at least a portion of beverage bottles handled by said beverage bottle handling machine to said beverage bottle filling machine;
- a beverage bottle closing machine being configured and disposed to close tops of filled beverage bottles a third conveyor arrangement being configured and disposed to convey filled beverage bottles to said beverage bottle closing machine;
- a beverage bottle packing machine being configured and disposed to pack closed, filled beverage bottles;
- a fourth conveyor arrangement being configured and disposed to convey closed, filled beverage bottles to said beverage bottle packing machine;
- a central control system being operatively connected to each of said machines to monitor and control the operation thereof;
- said beverage bottle filling machine comprising:
  - a rotor;
  - a rotatable vertical machine column;
  - said rotor being connected to said vertical machine column to permit rotation of said rotor about said vertical machine column;
  - a plurality of beverage bottle filling elements for filling beverage bottles with liquid beverage material being disposed on the periphery of said rotor;
  - each of said plurality of beverage bottle filling elements comprising a beverage bottle carrier being configured and disposed to receive and hold beverage bottles to be filled;
  - each of said plurality of beverage bottle filling elements being configured and disposed to dispense liquid beverage material into beverage bottles to be filled;
  - at least one liquid reservoir being configured to hold a supply of liquid beverage material;
  - at least one supply line being configured and disposed to connect said at least one liquid reservoir to said beverage bottle filling machine to supply liquid beverage material to said beverage bottle filling machine;
  - a first star wheel structure being configured and disposed to move beverage bottles into said beverage bottle filling machine; and
  - a second star wheel structure being configured and disposed to move beverage bottles out of said beverage bottle filling machine;
- said beverage bottle closing machine comprising:
  - a rotor;
  - a rotatable vertical machine column;
  - said rotor being connected to said vertical machine column to permit rotation of said rotor about said vertical machine column;
  - a plurality of closing devices being disposed on the periphery of said rotor;
  - each of said plurality of closing devices being configured and disposed to place closures on filled beverage bottles;
  - each of said plurality of closing devices comprising a beverage bottle carrier being configured and disposed to receive and hold filled beverage bottles;
  - a first star wheel structure being configured and disposed to move filled beverage bottles into said beverage bottle closing machine; and
  - a second star wheel structure being configured and disposed to move filled, closed beverage bottles out of said beverage bottle closing machine;
- said beverage bottle packing machine comprising:
  - a sorting arrangement being configured and disposed to sort and group beverage bottles into groups; and
  - a packaging arrangement being configured and disposed to package the groups of beverage bottles;
- said beverage bottle handling machine comprising:
  - a liquid dispensing device being configured and disposed to dispense an amount of clean water into beverage bottles to rinse observable, liquid-beverage contaminants from a substantial portion of the interior surface of the beverage bottles and gather the contaminants in the amount of clean water at the bottom of the beverage bottles;
  - a conveyor device comprising a first conveyor belt and a second conveyor belt, each being in the form of closed loops;
  - said first conveyor belt and said second conveyor belt being disposed adjacent one another to define a beverage bottle transport path there between;
  - said first conveyor belt and said second conveyor belt being configured and disposed to together hold and move beverage bottles there between in a transport direction along the beverage bottle transport path;
  - said conveyor device comprising a beverage bottle inlet area and a beverage bottle outlet area being disposed opposite ends of said conveyor device;
  - said conveyor device being configured and disposed to receive beverage bottles in their upright position at the beverage bottle inlet area upon dispensing of clean water into the beverage bottles by said liquid dispensing device;
  - said conveyor device being configured and disposed to transport the beverage bottles out of the conveyor device in their upright position at the beverage bottle outlet area;
  - said conveyor belts being configured and disposed to temporarily tilt beverage bottles being held and moved there between from their upright position to a tilted position in a plane perpendicular to the transport direction in between said beverage bottle inlet and outlet areas to gather the water in the beverage bottles in a bottom portion of the beverage bottles;
  - an observation device being configured and disposed to observe the water in tilted beverage bottles being held and moved by said conveyor belts to discern the presence of contaminants in the water in a sufficient quantity to contaminate liquid beverage material in a filled beverage bottle;
  - said observation device being configured and disposed to send beverage bottle observation information to said control system;
  - a separating device being configured and disposed to receive observed beverage bottles from said conveyor device and separate beverage bottles having a quantity of contaminants sufficient to contaminate liquid beverage material from beverage bottles being sufficiently free of contaminants;

said separating device being configured and disposed to receive beverage bottle separation information from said control system based on the observation information received by said control system from said observation device;

said separating device comprising a first separating conveyor and a second separating conveyor;

said first separating conveyor being configured and disposed to convey beverage bottles being sufficiently free of contaminants out of said beverage bottle handling machine for further handling in said beverage bottling plant; and said second separating conveyor being configured and disposed to convey beverage bottles being sufficiently contaminated out of said beverage bottle handling machine for disposal.

7. The beverage bottling plant according to claim 6, wherein each of said conveyor belts on the outside of their loops form inclined beverage bottle stop or clamping surfaces corresponding to the tilting angle of the beverage bottles, and in the vicinity of at least one of: the beverage bottle inlet and the beverage bottle outlet, there is at least one additional beverage bottle support element that supports the beverage bottles clamped between the conveyor belts during moving of the beverage bottles from at least one of: the upright position into the tilted position and the tilted position into the upright position.

8. The beverage bottling plant according to claim 7, wherein the at least one beverage bottle support element is located on one of the two conveyor belts; and the at least one beverage bottle support element is formed by at least one additional, driven, endless circulating auxiliary or support belt.

9. The beverage bottling plant according to claim 8, wherein the at least one auxiliary or support belt is driven in the same direction of rotation as the conveyor belts and at the same speed as the conveyor belts; and the conveyor belts are pivoted in a guide manner on guides so that the beverage bottles clamped between the conveyor belts are tilted at least once between the beverage bottle inlet and the beverage bottle outlet.

10. The beverage bottling plant according to claim 9, wherein the orientation of the guide planes of the guides for the conveyor belt lengths that form the conveyor line change at least once between the beverage bottle inlet and the beverage bottle outlet from a vertical orientation into an orientation that is inclined with respect to the vertical and back into the vertical orientation; and the orientations of the guide planes of the guides for the conveyor belt lengths that form the conveyor line change to the same degree along this conveyor line; and the conveyor belts are chains with clamping jaws provided on chain links.

11. A method of operating a beverage bottling plant for filling beverage bottles with liquid beverage material, said method comprising the steps of:

moving beverage bottles to a beverage bottle handling station;

dispensing with a liquid dispensing device an amount of liquid into beverage bottles and rinsing observable, liquid-beverage contaminants from a substantial portion of the interior surface of the beverage bottles and gathering the contaminants in the amount of liquid at the bottom of the beverage bottles;

receiving beverage bottles in their upright position at a beverage bottle inlet area into a conveyor device from said liquid dispensing device;

holding and moving beverage bottles in said conveyor device;

tilting beverage bottles during the movement thereof in said conveyor device and gathering the liquid in a bottom portion of the beverage bottles;

observing with an observation device the liquid in the tilted beverage bottles and discerning the presence of contaminants in the liquid in a sufficient quantity to contaminate liquid beverage material in a filled beverage bottle;

sending beverage bottle observation information from said observation device to a control system;

moving beverage bottles out of said conveyor device and into a separating device;

receiving with said separation device observation information from said control system and separating beverage bottles having a quantity of contaminants sufficient to contaminate liquid beverage material from beverage bottles being sufficiently free of contaminants;

moving beverage bottles being sufficiently free of contaminants out of said beverage bottle handling machine to a first location for further handling in said beverage bottling plant;

moving beverage bottles being sufficiently contaminated out of said beverage bottle handling machine to a second location other than said first location;

moving beverage bottles being sufficiently free of contaminants to a filling machine and filling the beverage bottles with a liquid beverage material in said filling machine;

moving filled beverage bottles to a closing machine and closing filled beverage bottles with a closure in said closing machine; and moving filled, closed beverage bottles to a packing machine and sorting, grouping, and packaging filled, closed beverage bottles in packages.

12. The method of operating a beverage bottling plant according to claim 11, wherein the containers are pivoted during transport on the conveyor line with their container axis FA in a plane perpendicular to the transport direction for the inspection.

13. The method of operating a beverage bottling plant according to claim 12, wherein the observation of the beverage bottles is performed optoelectrically using at least one light source and at least one optoelectric sensor element comprising one of: a light detector or a camera system.

14. The method of operating a beverage bottling plant according to claim 13, wherein during the observation, the beverage bottles are located with the area of the beverage bottle to be inspected in the light path between the at least one light source and the at least one optoelectric sensor element.

15. The method of operating a beverage bottling plant according to claim 14, wherein the area of the beverage bottle to be inspected is a bottom area that is adjacent to a peripheral wall of the beverage bottle.

16. The method of operating a beverage bottling plant according to claim 15, wherein for beverage bottles with a concavely curved beverage bottle bottom on the underside of the beverage bottle, the light beam of the at least one light source is directed onto the concave bottom area of the beverage bottles so that the light beam that penetrates the beverage bottle strikes the sensor element that is located laterally with respect to the beverage bottle.

17. The method of operating a beverage bottling plant according to claim 16, wherein for the observation, the beverage bottles are each filled with a precisely measured quantity of liquid; and the light beam from the at least one light source is reflected by total reflection on the surface of the liquid to the sensor element.

18. The method of operating a beverage bottling plant according to claim 17, wherein a signal that corresponds to the condition of the respective beverage bottle is produced from at least one of: the brightness and the spectrum of the light that strikes the sensor element; and after the observation and during the transport in the conveyor device, the beverage bottles are returned to their upright position.

19. The method of operating a beverage bottling plant according to claim 18, wherein the beverage bottles are pivoted with their beverage bottle axis by an angle that is one of: substantially less than 45° and approximately 20°-25°; and the beverage bottles are made of one of: glass, a translucent or transparent plastic, and PET.

* * * * *